(12) United States Patent
Metaxas et al.

(10) Patent No.: US 7,466,848 B2
(45) Date of Patent: Dec. 16, 2008

(54) METHOD AND APPARATUS FOR AUTOMATICALLY DETECTING BREAST LESIONS AND TUMORS IN IMAGES

(75) Inventors: Dimitris N. Metaxas, North Brunswick, NJ (US); Anant Madabhushi, Philadelphia, PA (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 606 days.

(21) Appl. No.: 10/736,455

(22) Filed: Dec. 15, 2003

(65) Prior Publication Data

US 2005/0027188 A1 Feb. 3, 2005

Related U.S. Application Data

(60) Provisional application No. 60/433,028, filed on Dec. 13, 2002, provisional application No. 60/439,031, filed on Jan. 10, 2003.

(51) Int. Cl.
*G06K 9/00* (2006.01)
*G06K 9/34* (2006.01)
*A61B 5/05* (2006.01)

(52) U.S. Cl. ............... 382/128; 382/173; 382/181; 600/410

(58) Field of Classification Search .......... 328/128; 600/410
See application file for complete search history.

(56) References Cited

U.S. PATENT DOCUMENTS

| | | | | |
|---|---|---|---|---|
| 5,081,689 A | * | 1/1992 | Meyer et al. | 382/199 |
| 5,239,596 A | * | 8/1993 | Mahoney | 382/180 |
| 5,669,382 A | * | 9/1997 | Curwen et al. | 600/425 |
| 6,078,680 A | * | 6/2000 | Yoshida et al. | 382/128 |
| 6,138,045 A | * | 10/2000 | Kupinski et al. | 600/425 |
| 6,249,594 B1 | * | 6/2001 | Hibbard | 382/128 |
| 6,385,332 B1 | * | 5/2002 | Zahalka et al. | 382/128 |
| 6,591,004 B1 | * | 7/2003 | VanEssen et al. | 382/154 |
| 6,690,816 B2 | * | 2/2004 | Aylward et al. | 382/128 |
| 6,909,913 B2 | * | 6/2005 | Vining | 600/407 |
| 7,187,800 B2 | * | 3/2007 | Hibbard | 382/173 |
| 2001/0044576 A1 | * | 11/2001 | Vining | 600/416 |

(Continued)

OTHER PUBLICATIONS

Rafael C. Gonzalez, Digital Image Processing, Nov. 9, 2001, Prentice Hall, 2/E, p. 79, p. 245.*

(Continued)

*Primary Examiner*—Jingge Wu
*Assistant Examiner*—Max Shikhman
(74) *Attorney, Agent, or Firm*—McCarter & English, LLP

(57) ABSTRACT

A method and apparatus for automatically detecting breast tumors and lesions in images, including ultrasound, digital and analog mammograms, and MRI images, is provided. An image of a breast is acquired. The image is filtered and contrast of the image is enhanced. Intensity and texture classifiers are applied to each pixel in the image, the classifiers indicative of the probability of the pixel corresponding to a tumor. A seed point is identified within the image, and a region of interest is grown around the seed point. Directional gradients are calculated for each pixel of the image. Boundary points of the region of interest are identified. The boundary points are passed as inputs to a deformable model. The deformable model processes the boundary points to indicate the presence or absence of a tumor.

39 Claims, 40 Drawing Sheets

U.S. PATENT DOCUMENTS

2003/0156748 A1* 8/2003 Fang et al. .................. 382/145

OTHER PUBLICATIONS

Rafael C. Gonzalez, Digital Image Processing, Nov. 9, 2001, Prentice Hall, 2/E, p. 79, p. 245.*

Kinnard, Separation of malignant and benign masses using maximum-likelihood modeling and neural networks, May 2002, SPIE, vol. 4684, pp. 733-741.*

Arger, et al., "Interreader Variability and Predictive Value of US Descriptions of Solid Breast Masses," Academic Radiology, vol. 8, No. 4, Apr. 2001, pp. 335-342.

Boulerroui, et al., "Segmentation of Ultrasound Images—Multiresolution 2D and 3D Algorithm Based on Global and Local Statistics," Pattern Recognition Letters 24 (2003), pp. 779-790.

Chou, et al., "Stepwise Logistic Regression Analysis of Tumor Contour Features for Breast Ultrasound Diagnosis," Ultrasound in Med. & Biol., 2001, vol. 27, No. 11, pp. 1493-1498.

Christopher, et al., "3-D Bayesian Ultra-sound Breast Image Segmentation Using the EM/MPM Algorithm," IEEE International Symposium on Biomedical Imaging, 2002, pp. 601-604.

Collaris, et al., "Automatic Detection of Closed Tumor Contours in Medical Ultrasound Images on the Basis of Level-Dependant Spatial Summation," Proceedings of the 18th Annual International Conference of the IEEE Engineering in Medicine and Biology Society, 1997, vol. 2, pp. 907-908.

Drukker et al., "Computerized Detection and Classification of Cancer on Breast Ultrasound," Academic Radiology, vol. 11, No. 5, May 2004, pp. 526-535.

Giger, "Computer-Aided Diagnosis of Breast Lesions in Medical Images," Computing in Medicine, 2000, pp. 39-45.

Guliato, et al., "Segmentation of Breast Tumors in Mammograms by Fuzzy Region Growing," Proceedings of the 20th International Conference of the IEEE Engineering in Medicine and Biology Society, 1998, vol. 20, No. 2, pp. 1002-1005.

Herlin, et al., "Stochastic Segmentation of Ultrasound Images," Proceedings of the 11th IAPR International Conference on Pattern Recognition, 1992, pp. 289-292.

Horsch, et al., "Automatic Segmentation of Breast Lesions on Ultrasound," Medical Physics, 2001, vol. 28(8), pp. 1652-1659.

Horsch, et al., "Performance of Computer-Aided Diagnosis in the Interpretation of Lesions on Breast Sonography," Academic Radiology, vol. 11, No. 3, Mar. 2004, pp. 272-280.

Muzzolini, et al., "Multiresolution Texture Segmentation With Application to Diagnostic Ultrasound Images," IEEE Transactions on Medical Imaging, vol. 12, No. 1, 1993, pp. 108-123.

Ogawa, et al., "Three Dimensional Ultrasonic Imaging for Diagnosis of Breast Tumor," IEEE Ultrasonics Symposium, 1998, vol. 2, pp. 1677-1680.

Ruggiero, et al., "Automatic Recognition of Malignant Lesions in Ultrasound Images by Artificial Neural Networks," Proceedings of 20th Annual International Conference of the IEEE Engineering in Medicine and Biology Society, 1998, vol. 20, No. 2, pp. 872-875.

Sivaramakrishnan, et al., "Texture Analysis of Lesions in Breast Ultrasound Images," Computerized Medical Imaging and Graphics, 2002, vol. 26, pp. 303-307.

Xiao, et al., "Segmentation of Ultrasound B-Mode Images With Intensity Inhomogeneity Correction," IEEE Transactions on Medical Imaging, 2002, vol. 21, No. 1, pp. 48-57.

Yoshida, et al., "Segmentation of Liver Tumors in Ultrasound Images Based on Scale-Space Analysis of the Continuous Wavelet Transform," IEEE Ultrasonics Symposium, 1998, vol. 2, pp. 1713-1716.

Metaxas, et al., "Images Segmentation Based on the Integration of Markov Random Fields and Deformable Models," Third International Conference on Medical Image Computing and Computer-Assisted Intervention, 2000, pp. 256-265.

Cohen, et al., "A Finite Element Method Applied to New Active Contour Models and 3D Reconstruction From Cross Sections," International Conference on Computer Vision, 1990, pp. 587-591.

* cited by examiner

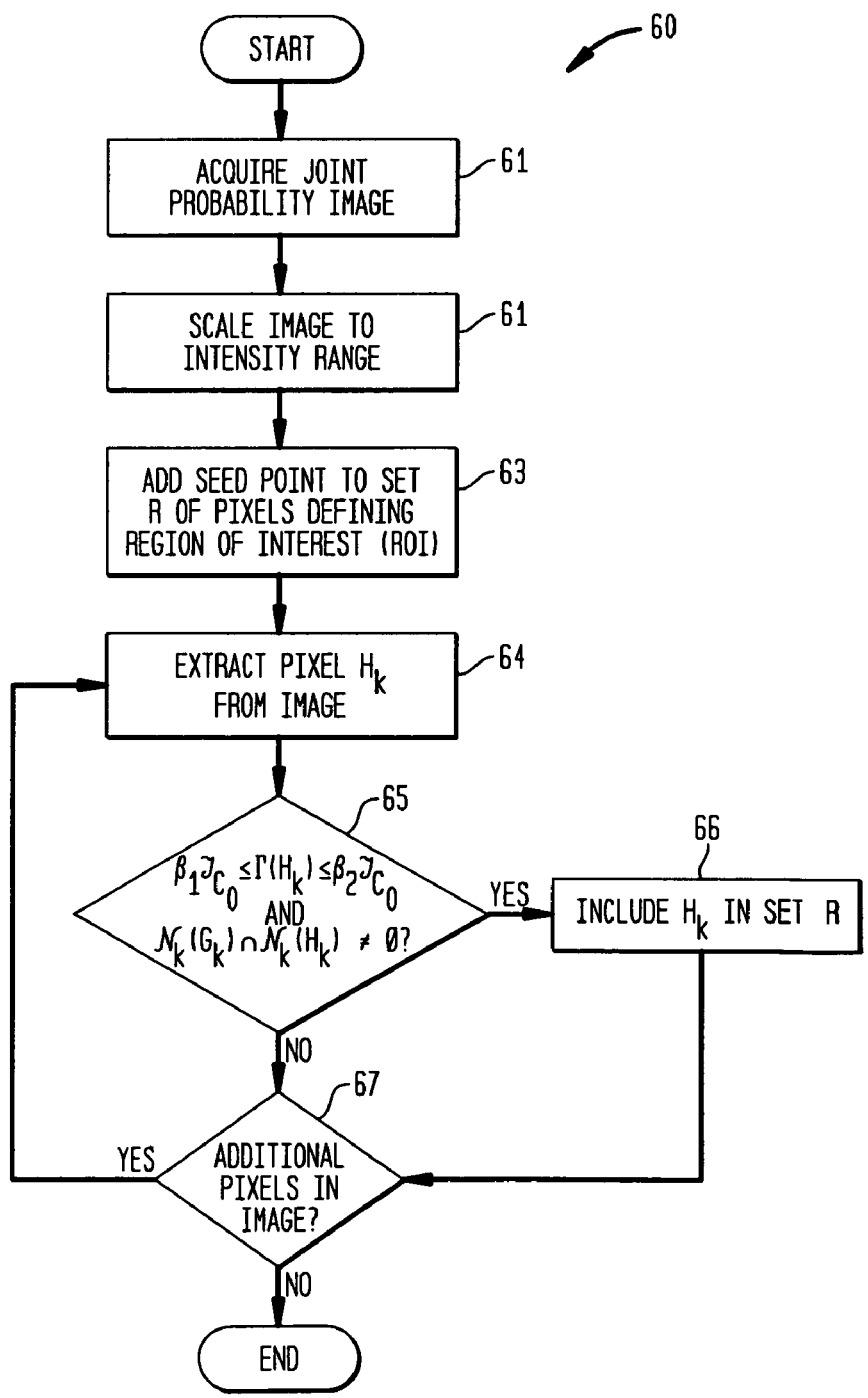

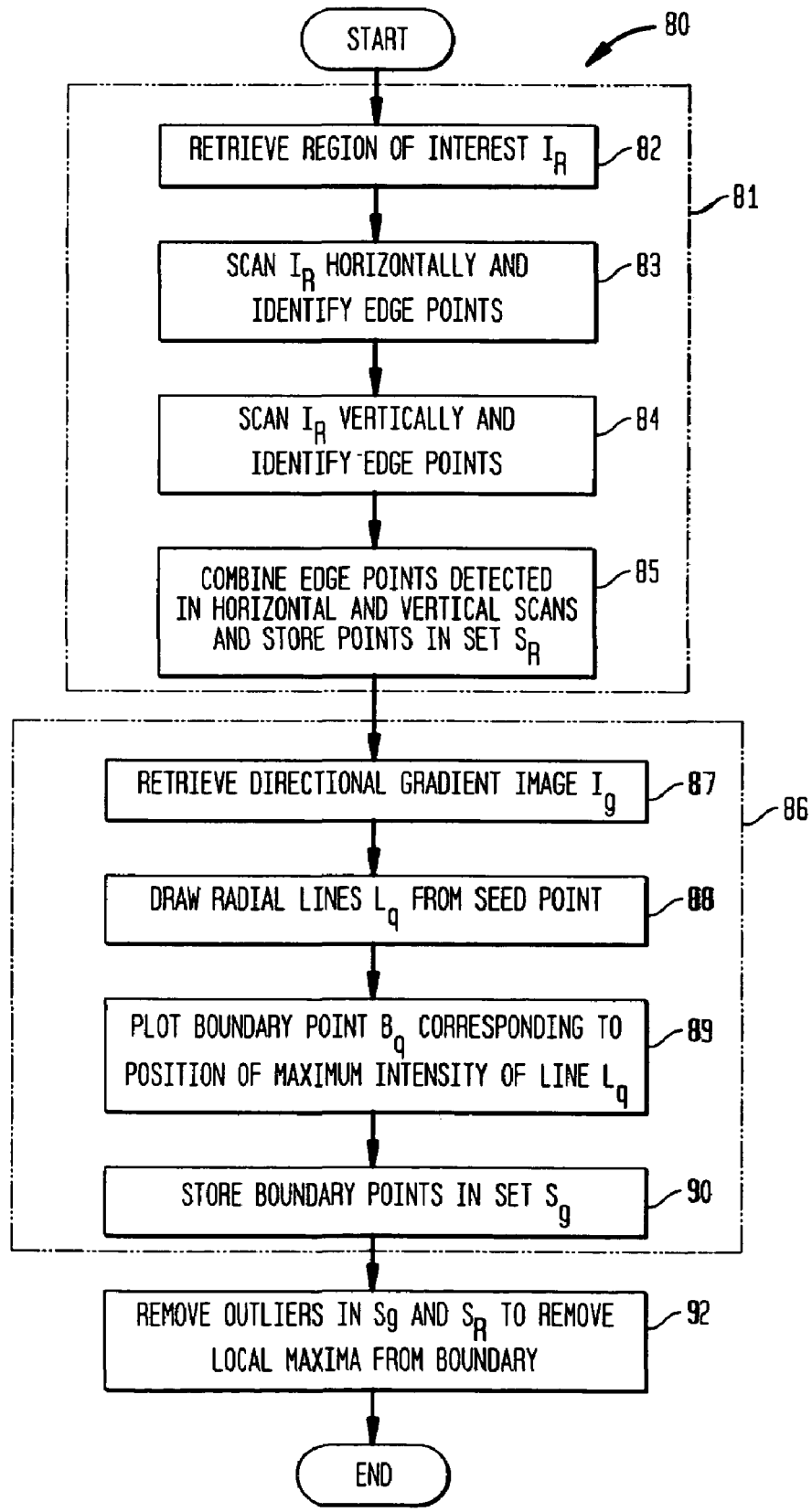

METHOD AND APPARATUS FOR AUTOMATICALLY DETECTING BREAST LESIONS AND TUMORS IN IMAGES

RELATED APPLICATIONS

This application claims the benefit of U.S. Provisional Application Ser. No. 60/433,028 filed Dec. 13, 2002 and U.S. Provisional Application Ser. No. 60/439,031 filed Jan. 10, 2003, the entire disclosures of which are both expressly incorporated herein by reference.

STATEMENT OF GOVERNMENT INTERESTS

The present invention was made under National Science Foundation Contract No. NSF 9820794. Accordingly, the Government may have certain rights to the present invention.

BACKGROUND OF THE INVENTION

1. Field of the Invention

The present invention relates to a method an apparatus for automatically detecting breast tumors and lesions in images. More specifically, the present invention relates to a method and apparatus for automatically segmenting, classifying, and detecting breast lesions in ultrasound, digital and analog mammogram, and magnetic resonance imaging (MRI) images.

2. Related Art

Breast cancer is the most frequently diagnosed malignancy and the second leading cause of mortality in women. In the last decade, ultrasound imaging, along with digital mammography, has become the standard for breast cancer diagnosis. Mammography is the most effective method for early detection of breast cancer, and periodic screening of asymptomatic women reduces the mortality rate. Typically, the first step in breast cancer detection is a screening mammogram, which comprises a low-dose x-ray examination on asymptomatic women. This can be followed by a diagnostic mammogram, which is an x-ray examination done to evaluate a breast complaint or to investigate an abnormality found during a physical examination or screening mammogram. Breast ultrasound is sometimes used to evaluate breast abnormalities that are found during screening mammography, diagnostic mammography, or a physical exam. If a suspicious object is found in the ultrasound image, a surgical biopsy or core needle biopsy is then recommended.

Most ultrasound and digital mammograms are manually interpreted by radiologists. However, manual interpretation is often inaccurate, and can fail to detect the presence of breast tumors and lesions. For example, between 10-30% of women who have breast cancer and undergo mammography have negative mammograms. In about two-thirds of these cases, the radiologist failed to detect retrospectively evident cancer. Such misses have been attributed to the subtle nature of the visual findings, poor image quality, or fatigue and/or oversight by the radiologist.

Several algorithms have been developed which claim to automatically classify breast lesions in ultrasound images. However, such algorithms rely on manual delineation of the tumor boundaries, and do not automatically delineate such boundaries. Further, automatically detecting tumors and extracting lesion boundaries in ultrasound images and digital mammograms is difficult due to the specular nature and the variance in shapes and appearances of sonographic lesions, as well as shadowing artifacts and tumor-like structures in the image, such as glandular tissue, coopers ligaments, and sub-cutaneous fat. Such obstacles make it difficult to automatically determine the lesion area using conventional image processing and computer vision techniques alone.

Many of the aforementioned algorithms rely on a priori shape information of the organ or structure of interest in order to effectuate segmentation. For example, a priori shape information has been used to segment ventricular structures in echocardiograms. However, such algorithms are not suitable for detecting breast lesions, due to variances of lesion shapes and the fact that lesion margins are often poorly defined. Region-based methods have been developed (e.g., fuzzy connectedness) which use homogeneity statistics coupled with low-level image features such as intensity, texture, histograms, and gradient to assign pixels to objects. In such methods, if two pixels are similar in value and connected to each other in some sense, they are assigned to the same object. These approaches, however, do not consider any shape information. As a result, such methods cannot deal with shadowing artifacts, which are common in ultrasound images.

Some researchers have proposed hybrid segmentation techniques to detect breast lesions. These approaches seek to exploit the local neighborhood information of region-based techniques, and the shape and higher-level information of boundary-based techniques. However, without manual intervention, these hybrid techniques cannot automatically distinguish other structures in the sonogram, such as sub-cutaneous fat, coopers ligaments and glandular tissue, from the true lesion.

In recent years, automated ultrasonic lesion segmentation schemes have been proposed, including techniques that uses a combination of the maximum a posteriori (MAP) and Markov Random Field (MRF) methods to estimate ultrasound field distortions and label image regions based on the corrected intensity statistics. However, the imaging model breaks down in the presence of shadowing artifacts. Other approaches attempt to automatically extract and classify ultrasonic breast lesions using fuzzy reasoning. All the pixels in the image are initially classified as normal, tumor, or boundary using a LOG filter. Subsequently, three types of images are generated corresponding to the grade of the pixel. The extracted tumor region is then classified as malignant or benign. Such systems do not consider the problem of speckle noise, shadowing artifacts, or tumor-like structures such as glandular and fatty tissue in the image.

Accordingly, what would be desirable, but has not yet been provided, is a method and apparatus for automatically segmenting and detecting breast lesions and tumors in images, including ultrasound, MRI, and digital and analog mammogram images, without requiring human intervention.

SUMMARY OF THE INVENTION

The present invention provides a method for automatically detecting breast tumors and lesions in images, including ultrasound, digital mammogram, and MRI images. The method comprises the steps of acquiring an image of a breast; filtering the image to remove speckle and enhance contrast; applying texture and intensity classifiers to each pixel of the image, the classifiers corresponding to probabilities of the pixel belonging to a lesion or tumor; determining a seed point in the image; growing a region of interest around the seed point; calculating directional gradients for each pixel in the image; determining boundary points of the region of interest using the directional gradients; and processing the boundary points with a deformable model to determine the presence or absence of a tumor or lesion in the image.

The present invention provides an apparatus for automatically detecting breast tumors and lesions in images. A scanner, such as a digital mammogram scanner, an ultrasound scanner, or an MRI scanner, generates an image of a breast. A filter filters the image to remove speckle and enhance contrast of the image. A processor calculates and applies texture and intensity classifiers to each pixel of the image, the classifiers corresponding to probabilities of the pixel belonging to a lesion or tumor. The processor determines a seed point in the image, and grows a region of interest around the seed point. Directional gradients for each pixel of the image are calculated by the processor, and boundary points of the region of interest are determined. A deformable model processes the boundary points to determine the presence or absence of a tumor or lesion.

BRIEF DESCRIPTION OF THE DRAWINGS

These and other important objects and features of the invention will be apparent from the following Detailed Description of the Invention, taken in connection with the accompanying drawings, in which:

FIG. 8 is a flowchart showing the processing logic of block 60 of FIG. 1 in greater detail.

FIG. 12 is a flowchart showing the processing logic of block 80 in greater detail.

DETAILED DESCRIPTION OF THE INVENTION

Figure 1:
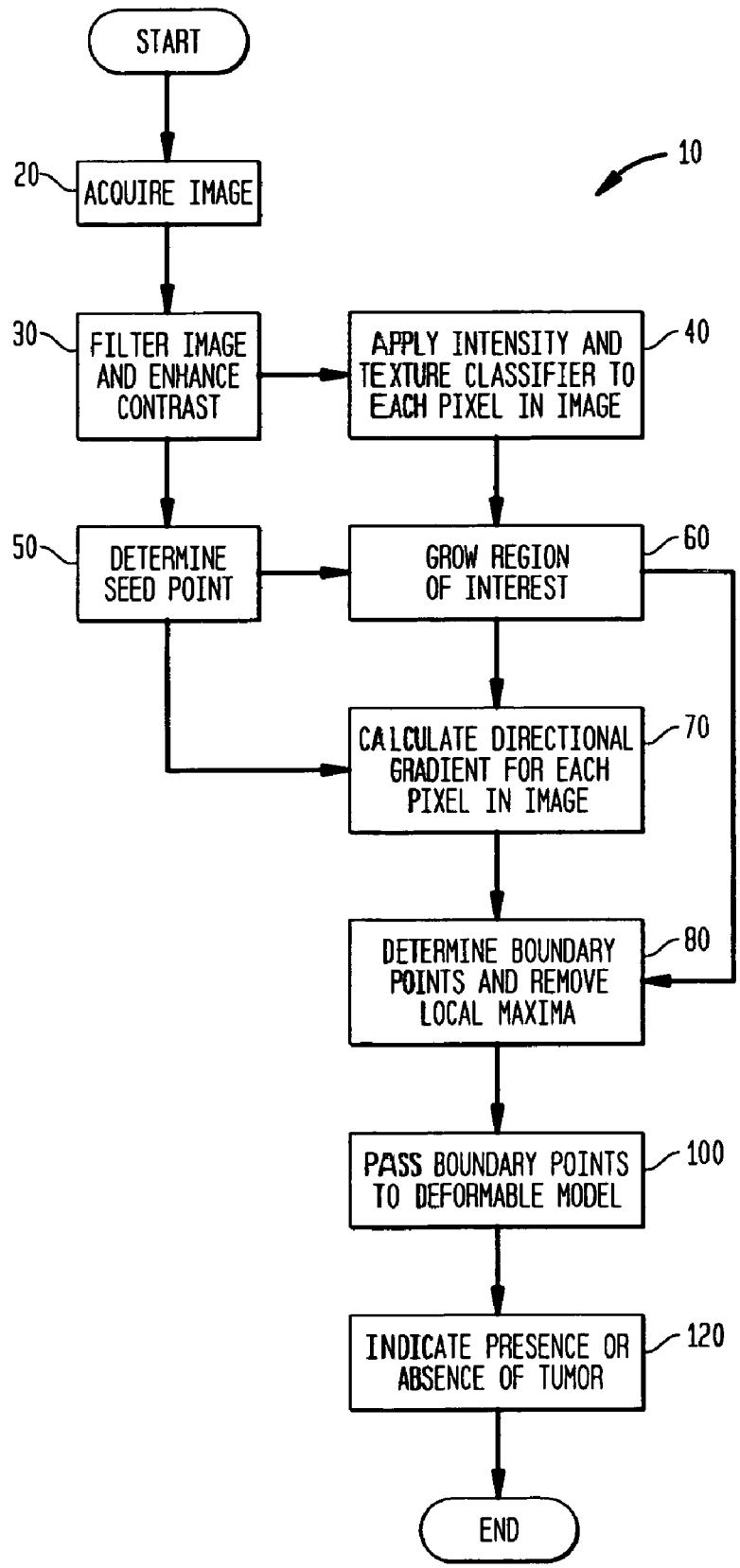
FIG. 1 is a flowchart showing overall processing logic performed by the present invention.

The present invention relates to a method and apparatus for automatically detecting breast tumors and lesions in images, including ultrasound, digital and analog mammograms, and MRI images. An image of a breast is acquired. The image is filtered and contrast of the image is enhanced. Intensity and texture classifiers are applied to each pixel in the image, the classifiers indicative of the probability of the pixel corresponding to a tumor. A seed point is identified within the image, and region of interest is grown around the seed point. Boundary points of the region of interest are identified. The boundary points are passed as inputs to a deformable model. The deformable model processes the boundary points to indicate the presence or absence of a tumor.

The present invention analyzes spatial distributions of various anatomic structures within a breast image, in addition to echogenicity of a lesion and its internal echo pattern, as three discriminating features for segmenting breast lesions and tumors in images. In sonographic images where the ultrasound transducer placed on the region of interest, the lesion appears roughly in the middle of the image. The skin appears as a bright linear echo near the top of the image. Sub-cutaneous fat typically appears just below the skin region. Coopers ligaments appear as septum-like or tent-like structures that arise from the surface of the breast parenchyma. The glandular region is separated from the sub-cutaneous fat by the superficial fascia. The ribs appear in the lower most part of the image and are associated with dense posterior acoustic shadowing.

Internal echo pattern refers to the texture or arrangement of echoes within a focal sonographic lesion. A non-homogeneous arrangement with few echoes, or even more, is suspicious for malignancy. A homogeneous internal echo pattern is more characteristic of sub-cutaneous fat. The echogenicity of a focal lesion is assessed in relation to the echo characteristics of adjacent tissues. The various grades of echogenicity are stated in reference to known structures, i.e., fat and glandular tissue. If a focal lesion appears less echogenic than fat, it is described as "almost anechoic." Such a lesion would appear darker than the surrounding fatty tissue. A "hypoechoic" focal lesion is less echogenic than glandular structures but more echogenic than fat (i.e., it appears darker than the glandular tissue but lighter than the fatty tissue). "Isoechoic" closely approximates the echogenicity of the glandular structures, while "hyperechoic" is used when the focal lesions appear brighter than the surrounding glandular tissue. Malignant lesions have been classified as "markedly hypoechoic" where there appear nodules that are very black compared to the surrounding isoechoic fat. "Anechoic" focal lesions have been identified as the hallmark of a cyst. Hence, both cysts and malignant lesion appear darker than glandular tissue or fat, which are usually either isoechoic or hyperechoic. Sub-cutaneous fat, on the other hand, is usually hypoechoic. These criteria are referred to in the relevant literature as the Stavros criteria, and are analyzed by the present invention to automatically segment and detect breast tumors and lesions in images.

FIG. 1 is a flowchart showing overall processing logic according to the present invention, indicated generally at 10, for automatically detecting breast tumors and lesions in images. Beginning in step 20, an image of breast is acquired. The image could be a digital mammogram, an ultrasound image, or an MRI image. Additionally, an analog image could be scanned and digitized. In step 30, the image is filtered, preferably using a Butterworth filter, and contrast of the image is enhanced. Of course, other filters could be used without departing from the spirit or scope of the present invention. The filtered and contrast-enhanced image is then utilized by steps 40 and 50.

In step 40, an intensity and texture classifier is applied to each pixel in the filtered and contrast-enhanced image. The classifier indicates the probability of the pixel corresponding to a tumor, and is generated using joint probability distribution functions for intensities and textures based upon empirical data. In step 50, a seed point within the filtered and contrast-enhanced image is generated. The seed point generated in step 50 and the joint intensity and texture probabilities calculated in step 40 are processed in step 60 to grow a region of interest around the seed point. In step 70, a directional gradient is calculated for each pixel in the image using the seed point generated in step 50 and the region of interest grown in step 60.

In step 80, boundary points of the region of interest grown in step 60 are determined based upon the directional gradients calculated in step 70. Local maxima are also removed from potential boundary points. In step 100, the boundary points are passed as inputs to a deformable model. In step 120, the outputs of the deformable model indicate the presence or absence of a tumor. Thus, as can be readily appreciated, the present invention allows for the automatic segmentation and detection of breast tumors and lesions in mammograms.

Figure 2:
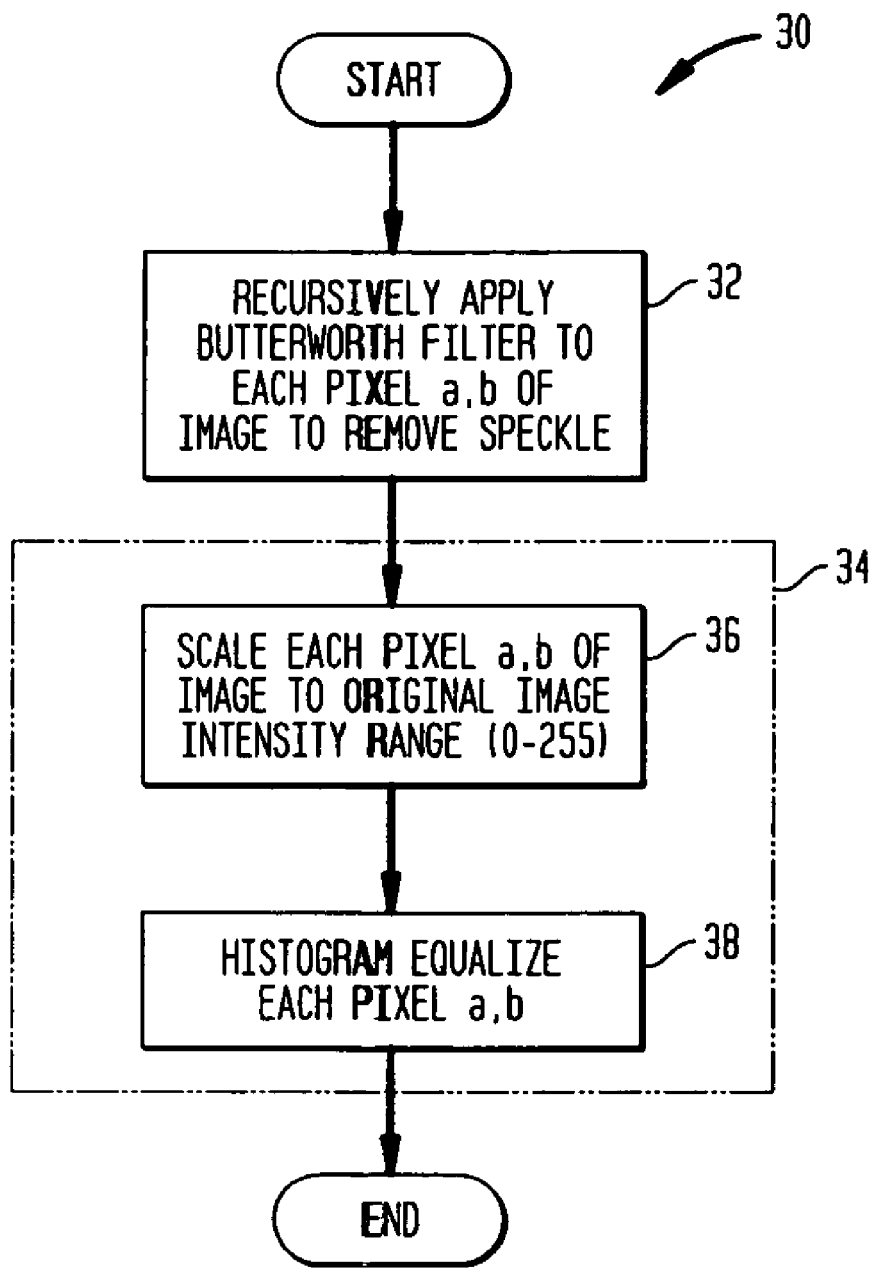
FIG. 2 is a flowchart showing the processing logic of block 30 of FIG. 1 in greater detail.

FIG. 2 is a flowchart showing the processing logic of block 30 of FIG. 1 in greater detail. In step 32, the acquired image is filtered to remove speckle using a second order Butterworth filter recursively applied to each pixel of the image. Speckle is a particular kind of noise which affects ultrasound images, and which can significantly reduce the quality and diagnostic usefulness of such images. Any known filter, such as a Gaussian filter, median filter, or anisotropic diffusion filter, can be used in place of a Butterworth filter without departing from the spirit or scope of the present invention.

An advantage of using a Butterworth filter is its low computational complexity. For kernel-based methods such as unsharp masking, and adaptive enhancement using local statistics, the computational times depend on the size of the image kernel. Hence, for a 5-by-5 kernel, 25 additions are required for a simple averaging operation. Importantly, Butterworth smoothing of the original image does not lead to an extensive loss of image details. The degree of enhancement can be adjusted by changing the coefficients of the low-pass filter, making the enhancement procedure very flexible. Further, the Butterworth filter can be easily extended to multiple dimensions without significant increase in computational complexity. The output of the low pass filter for the 2-dimensional case is computed using the following equations:

$$\overline{E}(a,b)=\gamma(\phi)\Psi(a,b)\phi+e^{-\phi}\overline{E}(a,b) \quad (1)$$

$$\Psi(a,b)=\gamma(\phi)=\gamma(\phi)\,\phi\rho(a,b)+e^{-\phi}\Psi(a-1,b) \quad (2)$$

$$\rho(a,b)=\gamma(\phi)E(a,b)\phi+e^{-\phi}\rho(a,b-1) \quad (3)$$

In the above equations $E(a,b)$ is the input image where a,b are the row and column positions of the pixels, $\overline{E}(a,b)$ is the output of the low-pass filter and $\rho(a,b)$ and $\Psi(a,b)$ are the results of the intermediate steps. The coefficient $\phi$ is proportional to the cut-off frequency, and $\gamma$ controls the magnitude of the filter. The value of $\phi$ is in the range of 0.1-1. The values of $\phi$ and $\gamma$ were varied and tested on a set of 21 training images that had been randomly selected from a database of images, and can be adjusted as desired. Optimally, the values of $\phi$ and $\gamma$ are set to values that result in the least amount of loss of image detail, while at the same time suppressing speckle.

In step 34, contrast of the image is enhanced in a two-step process comprising steps 36 and 38. First, in step 36, each pixel $\overline{E}(a,b)$ of the image is scaled to an original image intensity range of 0-255. The purpose of image enhancement is to adjust the display contrast and increase the edge sharpness of objects in the region of interest. As mentioned earlier, malignant tumors and benign cysts are typically anechoic or markedly hypoechoic, i.e., they constitute the darker parts of the image. This is different from digital mammography, where tumors and microcalcifications are typically the brighter regions in the image. Then, in step 38, each pixel is then histogram equalized to accentuate suspicious areas and enhance the boundary between lesions and the surrounding regions.

Figure 3A:
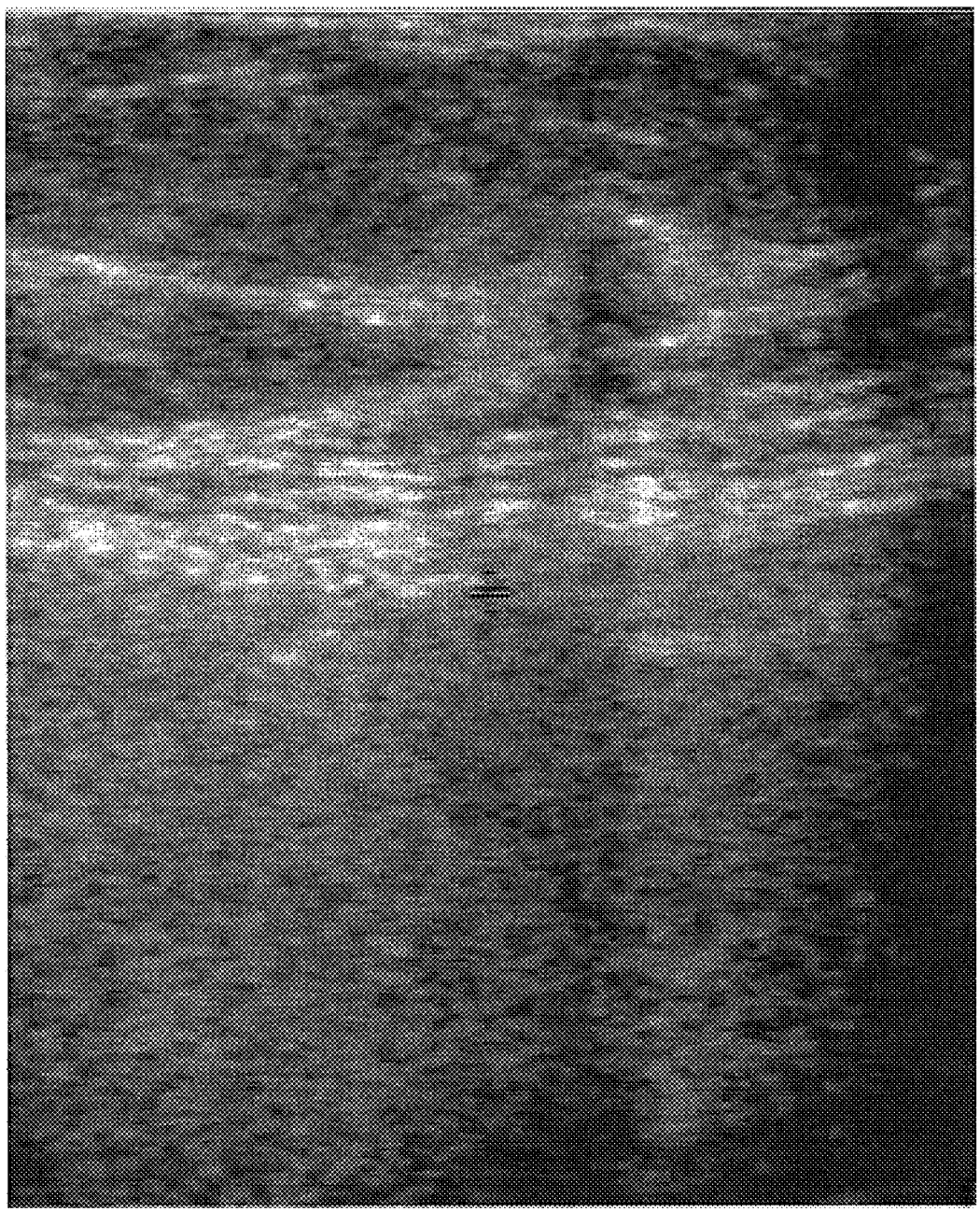
FIGS. 3a-3c are images showing image filtering and contrast enhancement achieved by the present invention.
Figure 3B:
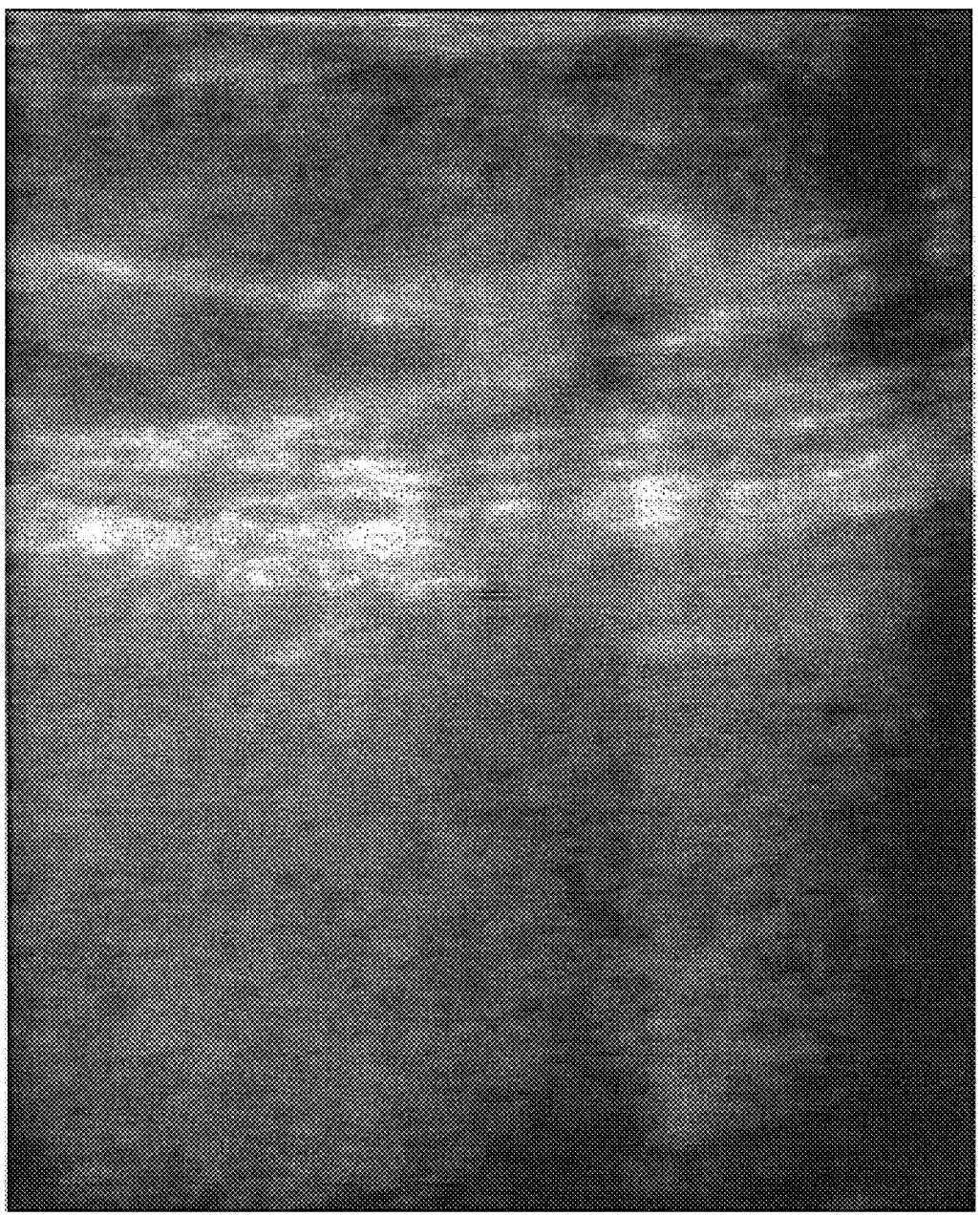
Figure 3C:
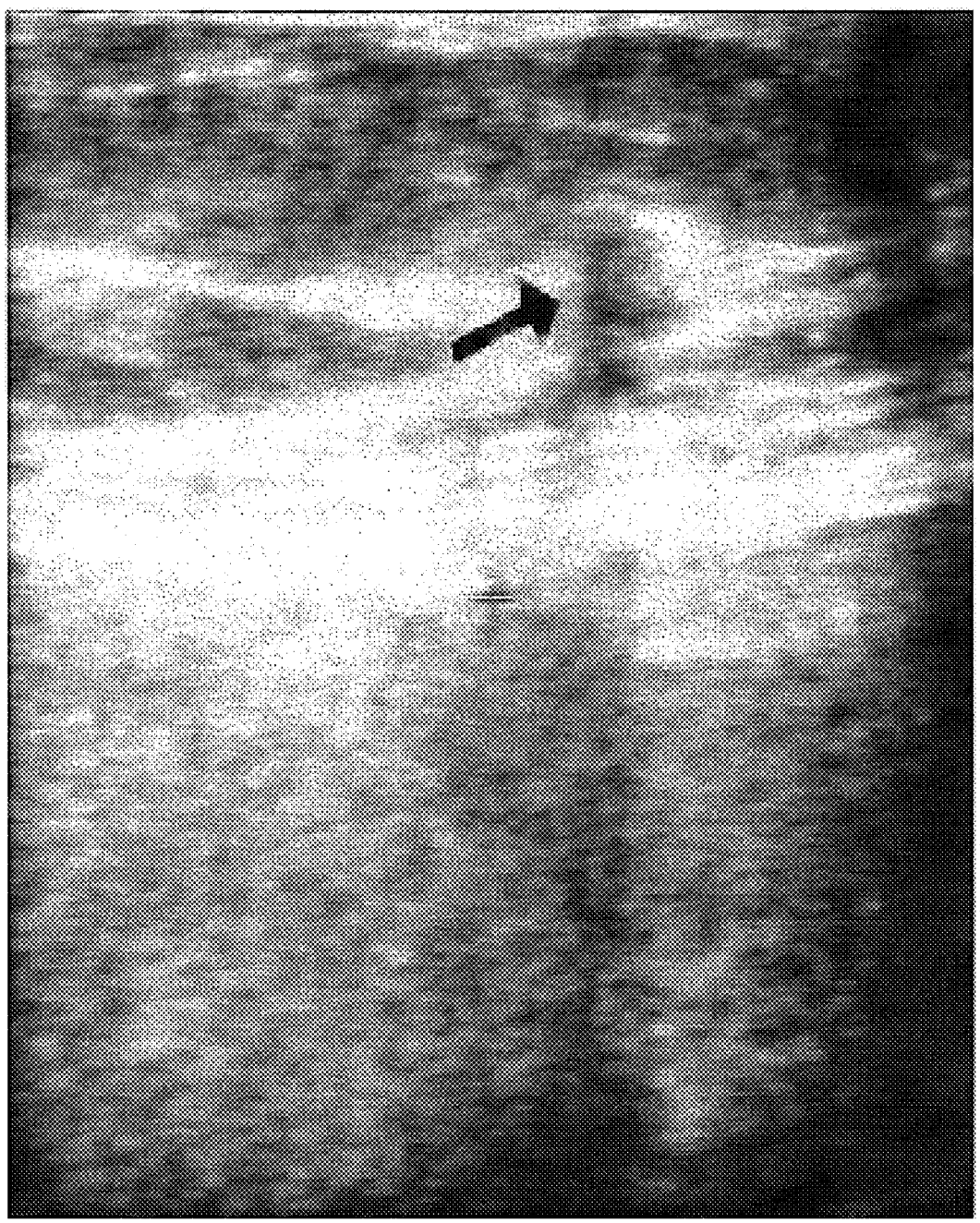

FIGS. 3a-3c are images showing image filtering and contrast enhancement achieved by the present invention. FIG. 3a shows the original image. FIG. 3b shows the result of Butterworth filtering. It can be seen that the speckle noise in FIG. 3a has been reduced in FIG. 3b. FIG. 3c shows the result of scaling and equalization to produce the contrast-enhanced image. The tumor, which is in the upper middle portion of the image, is barely visible in FIG. 3a but is clearly apparent in FIG. 3c. The arrow in FIG. 3c indicates the position of the tumor. As can be readily appreciated, the margins of the tumor have been enhanced.

Figure 4:
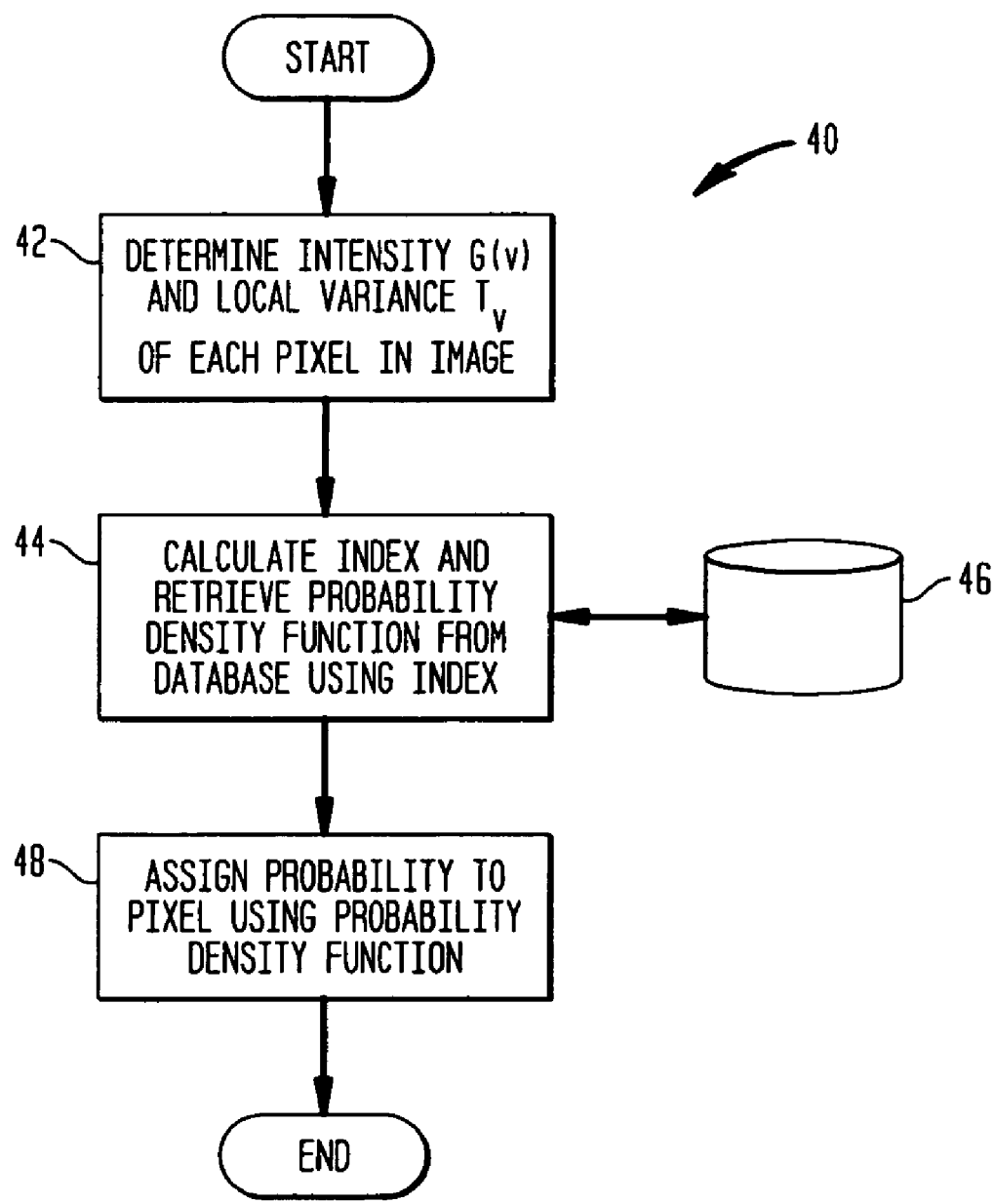
FIG. 4 is a flowchart showing the processing logic of block 40 of FIG. 1 in greater detail.

FIG. 4 is a flowchart showing the processing logic of block 40 of FIG. 1 in greater detail. In FIG. 4, the intensity and local variance (texture) of each pixel in the filtered and contrast-enhanced image is determined. As mentioned earlier, both intensity and texture have a high specificity for characterizing breast masses. Each pixel in the image is then assigned a probability of belonging to a tumor based on its texture and intensity, using probability distribution functions for texture and intensity.

Figure 5A:
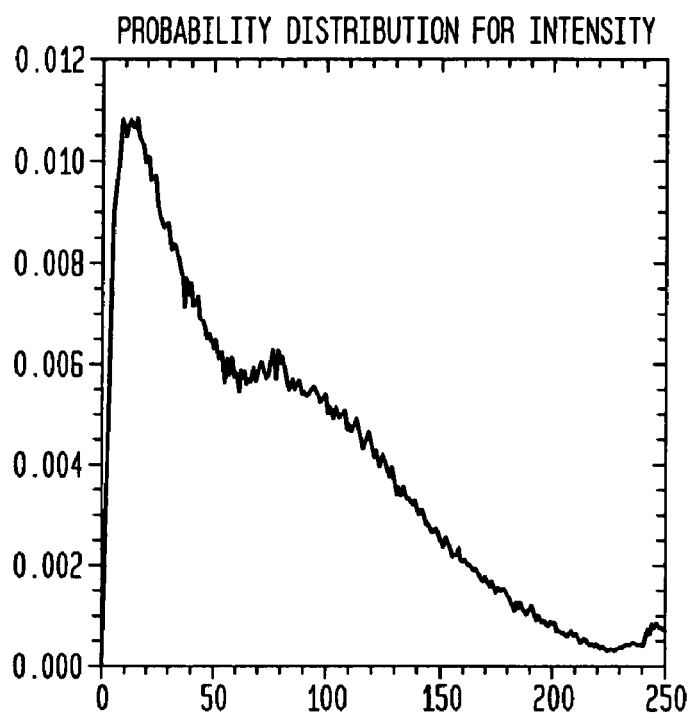
FIGS. 5a-5b are graphs showing sample probability distribution functions for intensity and texture.
Figure 5B:
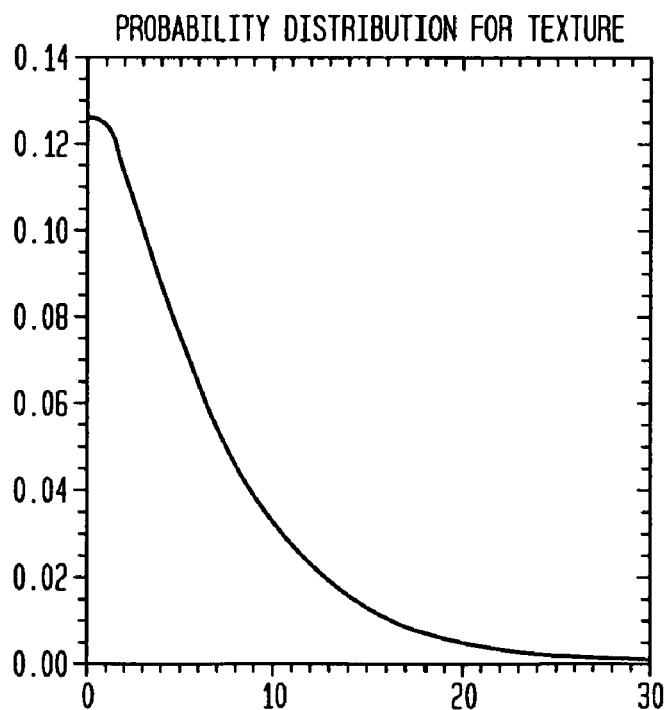

The probability distribution functions are stored in a database 46, and are based upon empirical data acquired from a set of 24 images chosen for purposes of training and testing. The lesions were manually cropped out from the training images and used for generating the probability distribution functions for intensity and texture. Sample probability distribution functions for intensity and texture computed from the training images are shown in FIGS. 5a and 5b, respectively.

In step 42 of FIG. 4, the texture of the pixel is calculated as the difference of the intensity of each pixel with the mean of its N nearest neighbors. The local variance texture feature captures the lesion's internal echo pattern, and can be defined as follows:

$$T_v = G(v) - \frac{1}{N}\sum_{\delta=0}^{N-1} W_\delta(v) \quad (4)$$

In equation 4, $T_v$ is the local variance of the pixel v, $G(v)$ is the pixel intensity and $W_\delta(v)$ refers to the intensity of the N nearest neighbors of v.

In step 44, the local variance and pixel intensity values are used as an index to retrieve the corresponding probability values from the database 46 of pre-computed texture and intensity probability density functions. The joint probability is then calculated according to the following equation and assigned to the pixel in step 48:

$$\Gamma(i,t)=\Gamma(i)\Gamma(t) \quad (5)$$

where $\Gamma(i),\Gamma(t)$ are the intensity and texture probabilities for each pixel and $\Gamma(i,t)$ is the joint probability that the pixel belongs to a tumor.

Figure 6A:
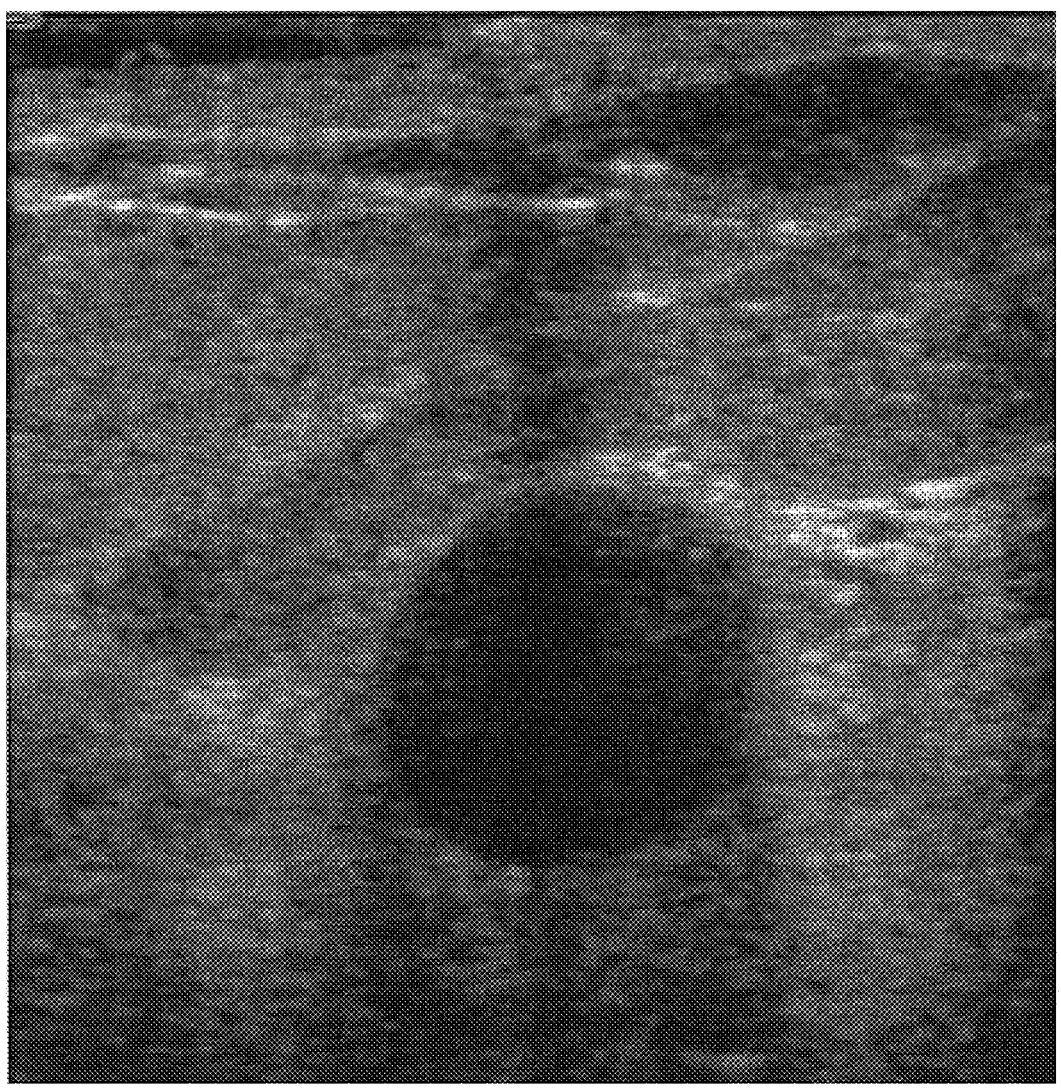
FIGS. 6a-6d are images showing pixel classification achieved by the present invention.
Figure 6B:
Figure 6C:
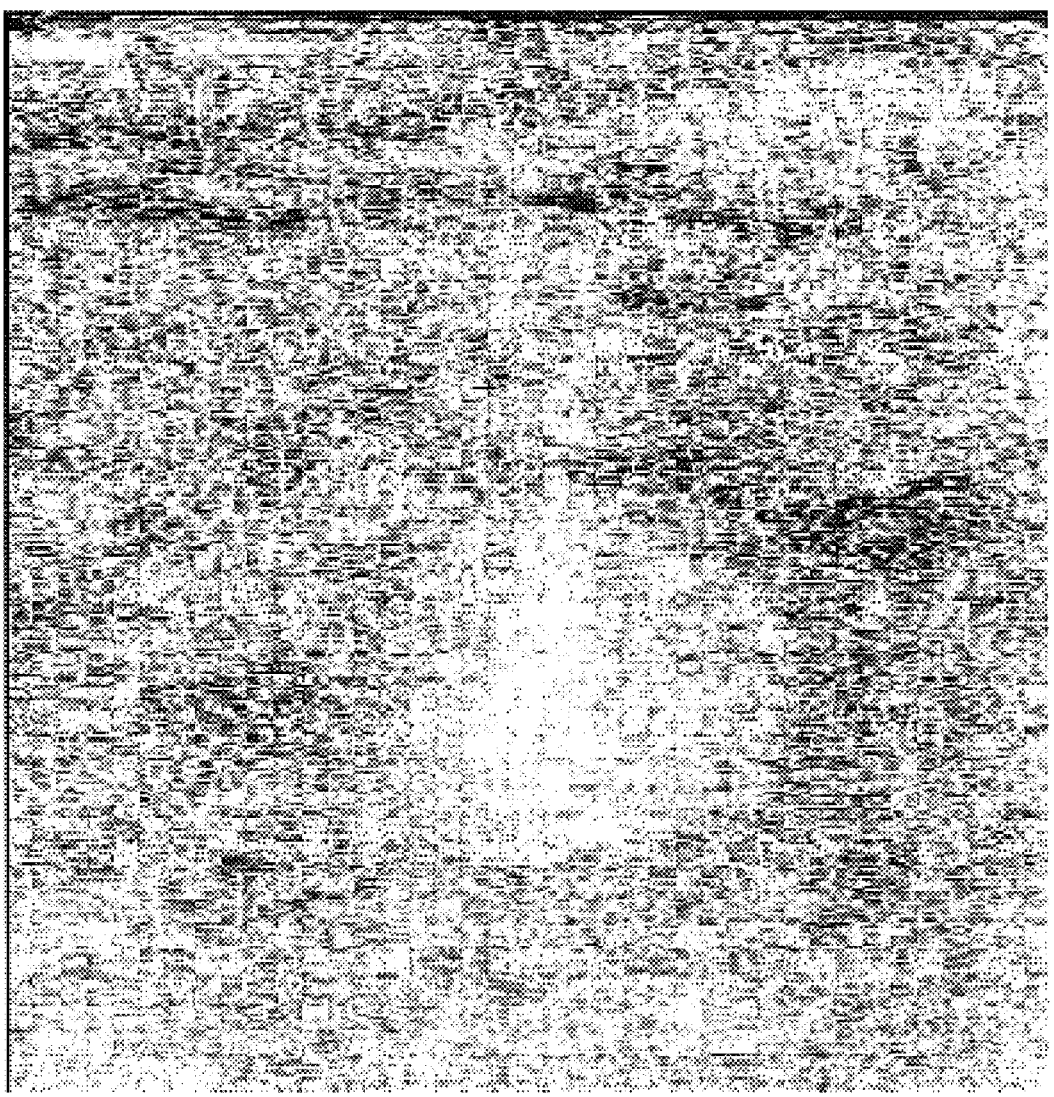
Figure 6D:
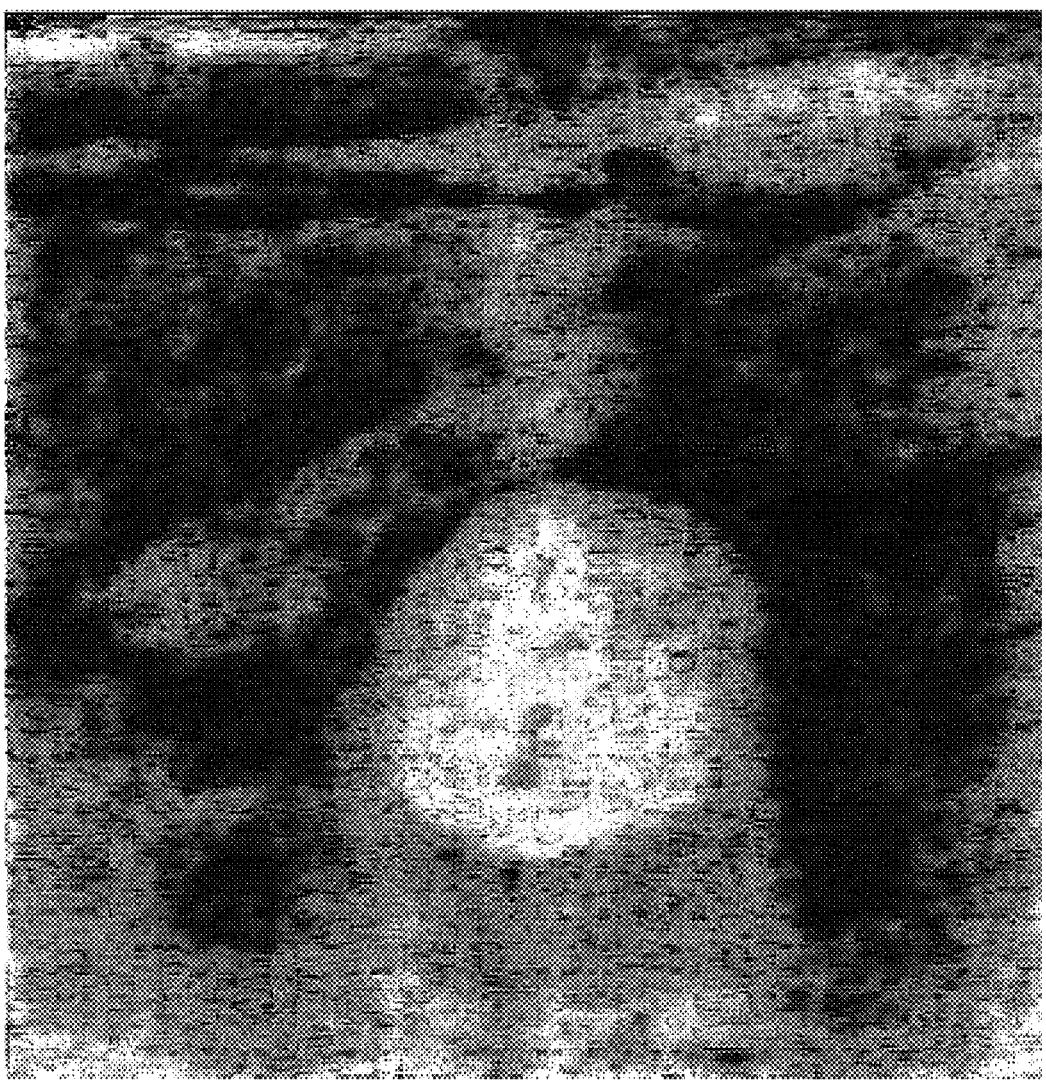

FIGS. 6a-6d are images showing pixel classification achieved by the present invention, using joint probabilities based upon pixel intensities and texture. FIG. 6a shows a sonogram with a large circular cyst in the lower portion of the image. The scaled probability images based upon intensity and texture are shown in FIGS. 6b and 6c. As can be seen in the joint probability image shown in FIG. 6d, most of the pixels having a high probability of belonging to a lesion (brighter pixels) have been identified correctly within the cyst.

Figure 7:
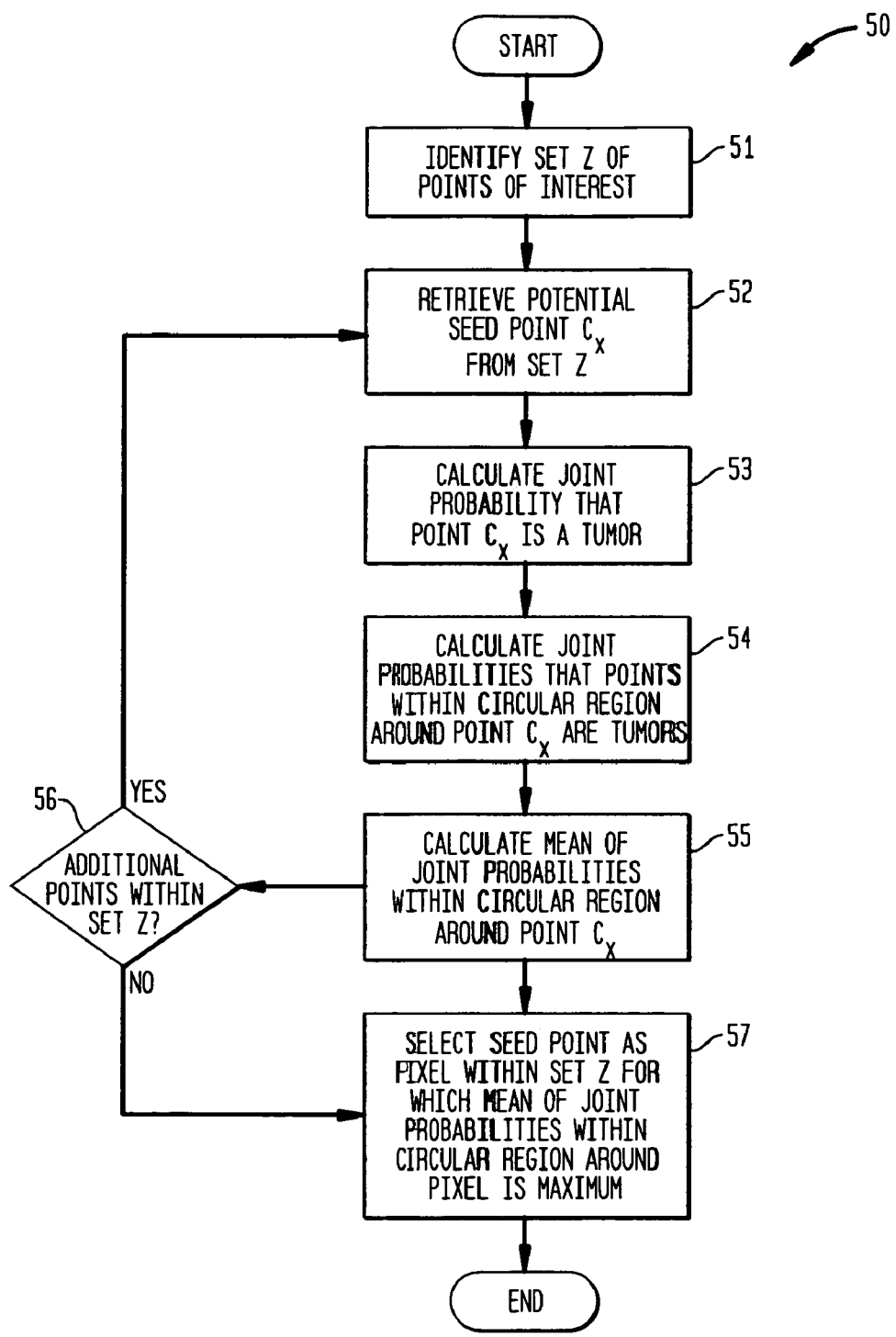
FIG. 7 is a flowchart showing the processing logic of block 50 of FIG. 1 in greater detail.

FIG. 7 is a flowchart showing the processing logic of block 50 of FIG. 1 in greater detail. In block 50, a seed point within a lesion area is automatically determined. The seed point is used for a region growing procedure to obtain an initial coarse segmentation of the lesion. When an ultrasound transducer is placed on a region of interest, the lesion usually appears in the middle of the image. Sub-cutaneous fat, glandular tissue, and skin typically appear in the upper portion of the image. In order to ensure that the seed point is not detected within one of these regions, the present, invention incorporates a distance constraint. Thus, pixels which are located toward the center of the image are more likely to belong to a tumor. Also, shadowing regions typically appear in the posterior part of the image. To eliminate points within the shadowing region that might be mistaken for the true seed point, the present invention incorporates spatial information about the potential seed. Thus, potential seeds that occur lower in the image are less likely to be tumor pixels than points that appear higher up in the image. As mentioned earlier, cysts and malignant tumors are usually anechoic or markedly hypoechoic, meaning that such formations are usually darker than the surrounding fatty and glandular tissue. To accommodate this difference, the present invention incorporates intensity information of the potential seed point. Further, texture information about the seed point is taken into account, since fatty tissue tends to be homogeneous and malignant lesions are usually non-homogeneous.

Beginning in step 51, a set Z of points of interest is identified. Assume that a random set of points $Z=\{C_0, C_1, C_2, \ldots, C_\zeta\}$ are in the image, which set contains the seed point $C_0$ lying within a region of interest. To extract $C_0$:

$$\forall \ C_x \in Z \qquad (6)$$

$$\tau_{C_x} = \frac{\Gamma_{C_x}(i, t) J_{C_x} Y_{C_x}}{d_{C_x}}$$

where $\Gamma_{C_x}(i,t)$ refers to the joint probability value that a potential seed point (pixel) $C_x$ belongs to a tumor. $J_{C_x}$ corresponds to the mean of the $\Gamma(i,t)$ value of pixels in a circular region around pixel $C_x$. $Y_{C_x}$ is the row position of $C_x$ and $d_{C_x}$ is the Euclidean distance between the seed point and the centroid of the image.

In step 52, a potential seed point $C_x$ is retrieved from set Z. Then, in step 53, the joint probability $\tau_{C_x}$ is computed for $C_x$. In step 54, the joint probabilities of points within a circular region around $C_x$ are calculated, and in step 55, the mean of these probabilities is calculated. A determination is made in step 56 as to whether additional potential seed points exist within set Z. If a positive determination is made, step 52 is re-invoked. Otherwise, in step 57, the true seed point is selected as that $C_x$ for which $\tau_{C_x}$ is maximum.

FIG. 8 is a flowchart showing the processing logic of block 60 of FIG. 1 in greater detail. When a seed point has been identified, a region of interest containing the tumor region is grown around the seed point. The region growing operation is performed on the joint probability image generated by the present invention and described earlier with reference to FIGS. 4-6d. Beginning in step 61, the joint probability image is acquired, and then scaled into the intensity range in step 62. Pixels in the vicinity of the seed point are grouped together based on their value and their connectivity. R is the set containing all the region pixels ($G_k$) and corresponds to the region of interest. In step 63 the seed point is added to the region of interest, such that R only contains the seed pixel $C_0$. A pixel $H_k$ is extracted from the image in step 64. In step 65, a determination is made as to whether the pixel $H_k$ should be included in the region of interest. A pixel $H_k$ can be included in R if, for $\forall G_k \in \{R\}$, $H_k$ satisfies the following conditions:

$$if \beta_1 J_{C_0} \leq \Gamma(H_k) \leq \beta_2 J_{C_0} \text{ and } N_k(G_k) \cap N_k(H_k) \neq \emptyset \qquad (7)$$

where $\beta_1, \beta_2$ are the thresholds for determining the range of pixel values in the joint probability image to be included in the region. N denotes the square neighborhood around the pixel under consideration and K denotes the type of connectivity used. If a positive determination is made, the pixel $H_k$ is included in the region of interest in step 66. Otherwise, a determination is made in step 67 as to whether additional pixels exist in the image. If so, step 64 is re-invoked so that additional pixels can be processed. When the region growing operation begins, $J_{C_0}$ is used instead of $\Gamma(C_0)$ in order to prevent the operation from being dependent on the value of a single point.

The values of $\beta_1, \beta_2$ and N were calculated based upon empirically data. A range of values for $\beta_1, \beta_2$ and N were used to test the output of the system for the 21 training images. Those values that gave a segmented region closest to the manually delineated lesion for a majority of the training images were selected. The same values were then used for all subsequent testing.

Figure 9A:
FIGS. 9a-9c are images showing seed generation and region-of-interest growth achieved by the present invention.
Figure 9B:
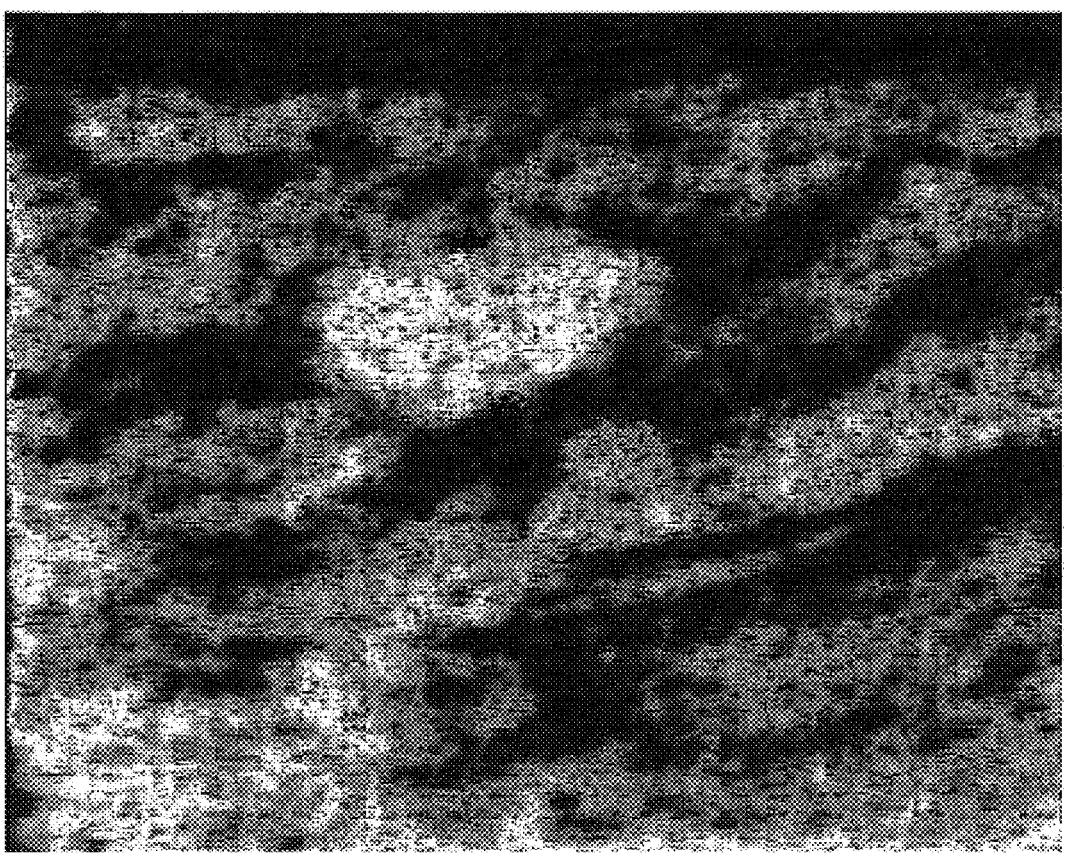
Figure 9C:
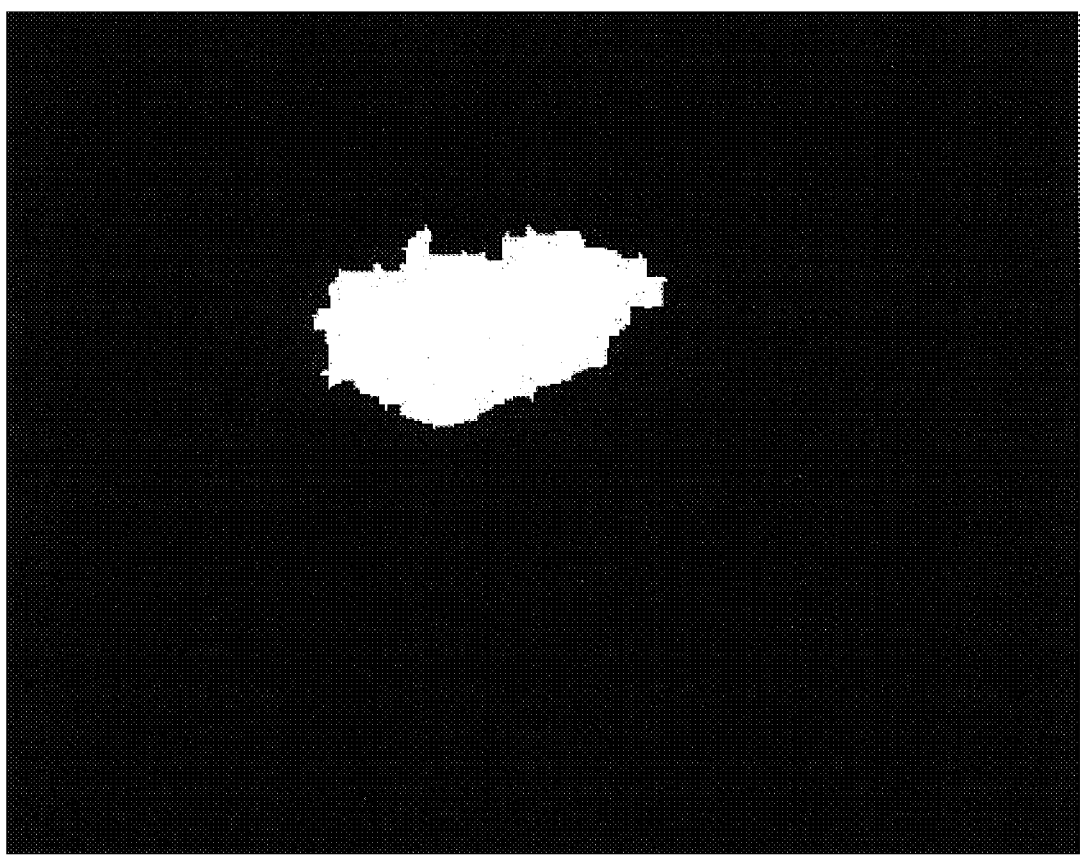

FIGS. 9a-9c are images showing seed generation and region-of-interest growth achieved by the present invention. FIG. 9a depicts the original image. FIG. 9b depicts the joint probability image based on texture and intensity. FIG. 9c shows the result of the region growing algorithm. The area returned by the region-growing algorithm ($I_R$) is used to determine a region of interest for finding boundary points. The extreme pixels of $I_R$ are used to determine the dimensions of the bounding box. The bounding box dimensions are scaled up by a factor ε to ensure that the true tumor region is included within it.

Figure 10:
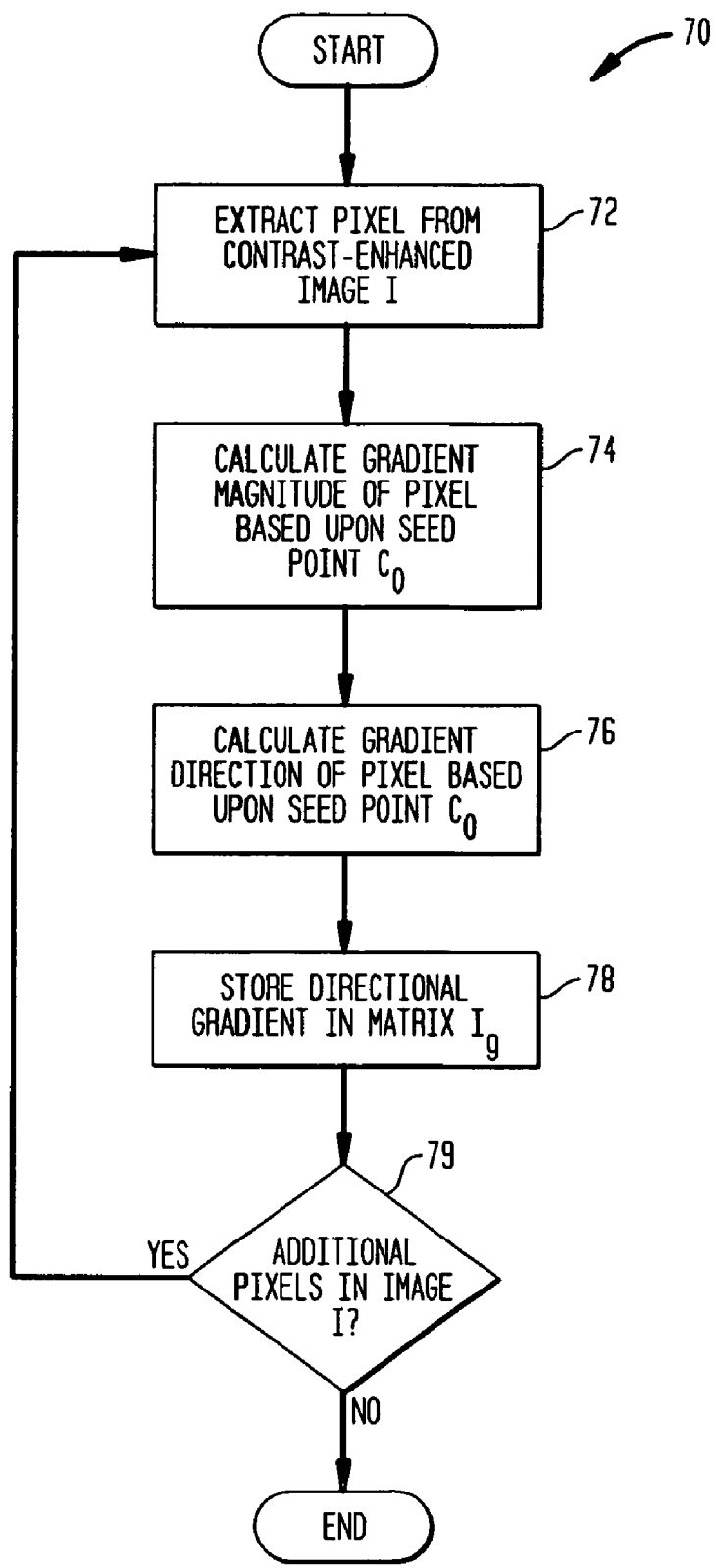
FIG. 10 is a flowchart showing the processing logic of block 70 of FIG. 1 in greater detail.

FIG. 10 is a flowchart showing the processing logic of block 70 of FIG. 1 in greater detail. In step 72, a pixel extracted from contrast-enhanced image I generated by the present invention. Then, in steps 72 and 74, a gradient magnitude and directional derivative of the contrast-enhanced image I is generated based on the seed point $C_0=(x_0, y_0)$. This is subsequently used for determining boundary points on the lesion margin. The directional gradient is stored in matrix $I_g$ in step 78, and is given by:

$$I_g = \frac{-\hat{F}}{\|\hat{F}\|} \text{ where } \hat{F} = \frac{\partial I}{\partial x}\tilde{n}_x + \frac{\partial I}{\partial y}\tilde{n}_y \qquad (8)$$

The spatial partial derivatives $$\frac{\partial I}{\partial x}, \frac{\partial I}{\partial y}$$

are computed from the contrast enhanced image I and the normalized derivatives $\tilde{n}_x, \tilde{n}_y$ are calculated as, $$\tilde{n}_x = \frac{\hat{x}}{\|\hat{x}+\hat{y}\|} \quad (9)$$

$$\tilde{n}_y = \frac{\hat{y}}{\|\hat{x}+\hat{y}\|} \quad (10)$$

where $\hat{x}=V_{x-x_0}$ and $\hat{y}=V_{y-y_0}$, $V_x, V_y$ are matrices having the same dimensions as I and containing the row and column positions of all the pixels in the image respectively. In step 79, a decision is made as to whether there are additional pixels in contrast-enhanced image I. If so, step 72 is re-invoked to process the additional pixels.

Thus, for every pixel in the contrast-enhanced image, the gradient magnitude of the pixel is calculated, as well as its direction. By incorporating information about the gradient direction and starting with a seed point within the tumor, it is possible to capture the lesion boundary better than by using only the gradient magnitude of the image.

Figure 11A:
FIGS. 11a-11c are images showing directional gradients generated by the present invention.
Figure 11B:
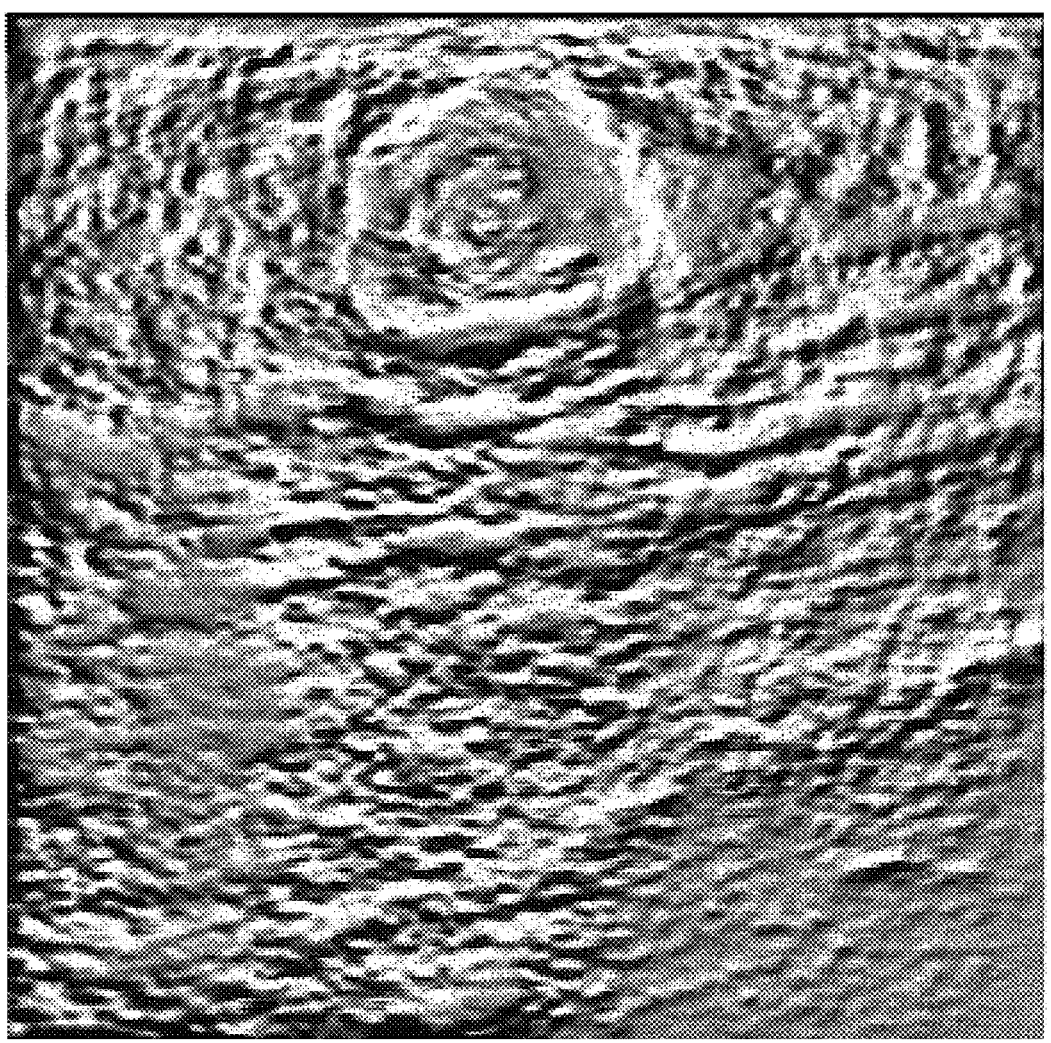
Figure 11C:
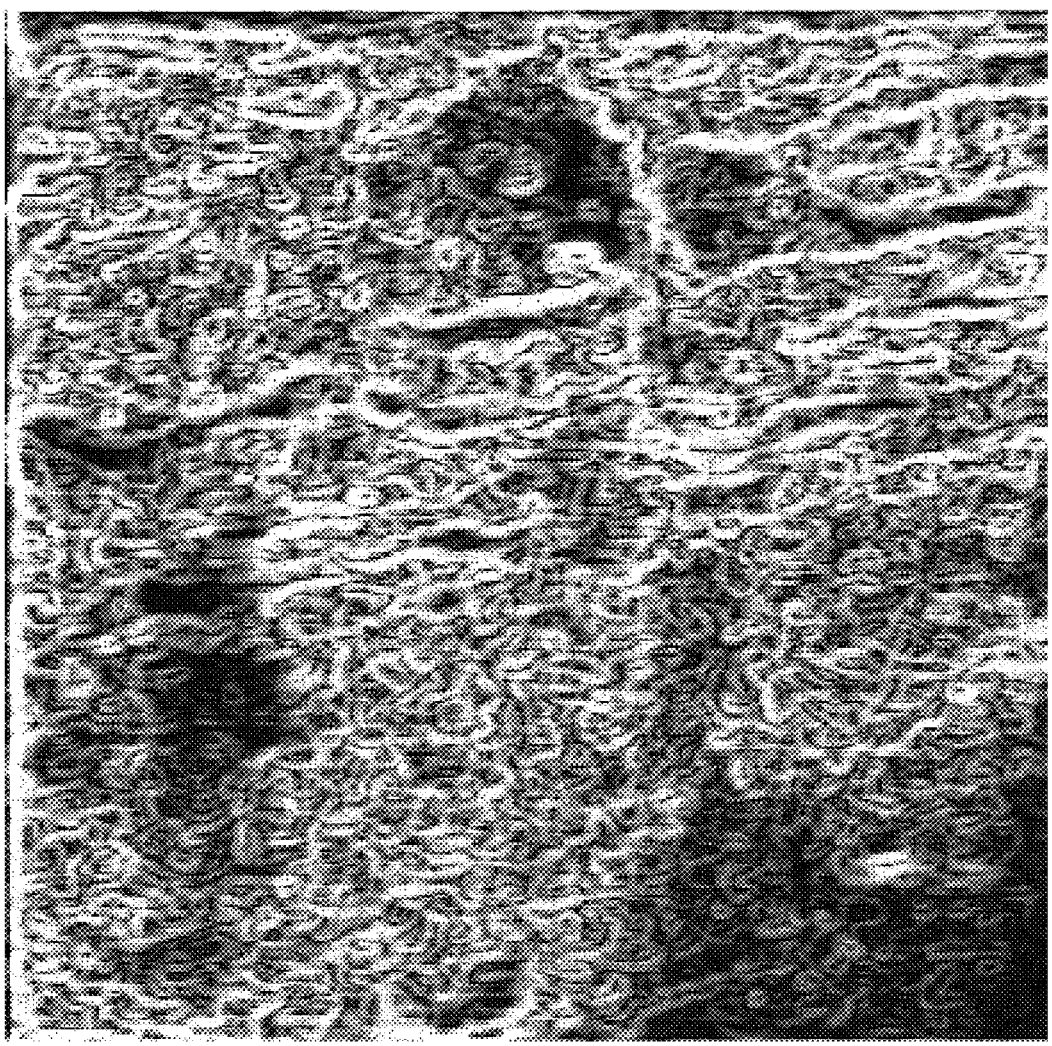

FIGS. 11*a*-11*c* are images showing directional gradients generated by the present invention. FIG. 11*a* shows the original image, and FIG. 11*b* shows its directional gradient. As can be seen, the margin of the tumor is more pronounced than the surrounding tissue in FIG. 11*b*. FIG. 11*c* shows the gradient magnitude of the original image, which shows less structure than the directional gradient of FIG. 11*b*.

FIG. 12 is a flowchart showing the processing logic of block 80 in greater detail. In block 80, the results of region growing ($I_R$) achieved in block 60 of FIG. 1, as well as the directional gradient image ($I_g$) generated in block 70 of FIG. 1, are used to find the boundary points of the lesion margin. This is shown in FIG. 12 as two boundary detection procedures 81 and 86.

In boundary detection procedure 81, $I_R$ is retrieved in step 82. Then, in steps 83 and 84, $I_R$ is scanned horizontally and vertically to determine edge points. On each scan, two edge points are detected. This is achieved by finding the positions of all non-zero pixels on each scan line and taking the first and last non-zero pixels as the edge points for that scan line. Boundary points detected from the horizontal and vertical scans are then combined in step 85, and stored in set $S_R$. Since it is not essential to obtain every single boundary point, this approach is used for its speed.

Figure 13A:
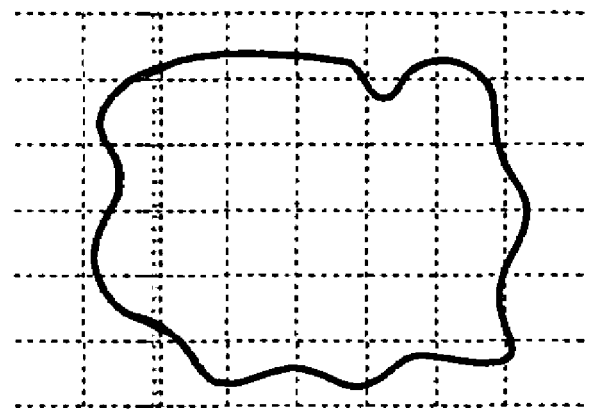
FIGS. 13a-13b are graphs illustrating boundary definition techniques achieved by the present invention.
Figure 13B:
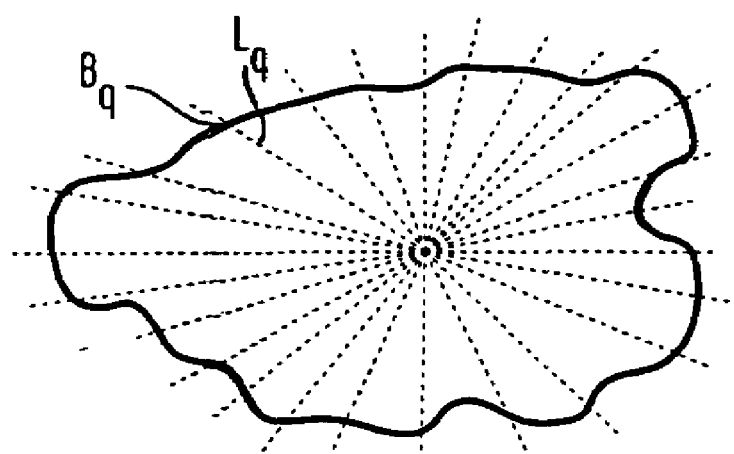

Boundary detection procedure 86 is then invoked. In step 87, the directional gradient image $I_g$ is retrieved. In step 88, radial lines $L_q$ are drawn outward from the seed point. Then, in step 89, boundary points $B_q$ are found and plotted as positions of maximum intensity on these lines. Each radial line contributes one boundary point. The boundary points are then stored in step 90 in set $S_g$. The procedure can be described as follows:

$$\forall L_q \text{ we find} \quad (11)$$

$$B_q = \max_{\phi}\{D_{q\phi}\}$$

where $D_{q\phi} \in L_q$. Further, the boundary detection procedures can be illustrated graphically with reference to FIGS. 13*a*-*b*. FIG. 13*a* shows a sketch of how scanning is performed on $I_R$ to obtain the edge points. FIG. 13*b* shows how edge points are found in $I_g$.

Turning back to FIG. 12, in step 92, outliers and local maxima are removed from the boundary points detected by procedures 81 and 86. Due to inhomogeneities in the tumor region, some points within the region are included as boundary points in $I_g$. These points correspond to local maxima and must be eliminated. Similarly shadowing produces some outlier points. Denoting $S_g, S_R$ as the set of boundary points determined from $I_g, I_R$, we find the distance of every point in $S_g$ from every point in $S_R$:

$$\forall l \in S_g \text{ we find} \quad (12)$$

$$d_l = \min_{w}\|l - \hat{j}_w\|$$

where $j \in S_R$. A point v is considered an outlier if, $$d_v < \alpha \mu_l \quad (13)$$

where $\alpha$ is a predetermined constant, $d_v$ is the Euclidean distance between the point v and the seed point, and $\mu_l$ is the mean over all $d_l$. Thus, those points in $S_g$ that do not have a corresponding point in the proximity of any point in $S_R$ are removed. However, the steps described in equations 12 and 13 do not remove all the outliers. To remove the other outliers in $S_R$, a recursive refinement procedure is performed. The mean ($\xi$) of the Euclidean distance between the boundary points and the seed point $S_R$ is computed:

$$\xi = \frac{1}{\eta}\sum_{u=0}^{\eta}\|l_u - C_o\| \quad (14)$$

where $l_u \in S_g$ and $C_0$ is the seed point. Similar to equation 12, a pixel is considered as a local maxima, if it lies at a distance greater or lesser than a factor of the mean (denoted by $\alpha_{near}$ and $\alpha_{far}$). On every iteration, $\xi$ is re-computed and points are eliminated. The iteration stops when:

$$|\xi_{n+1} - \xi_n| < \partial \quad (15)$$

where $\xi_n$ is the value of the mean at iteration n and $\partial$ is a predetermined threshold. The optimal values for $\alpha_{near}$ and $\alpha_{far}$ were determined empirically after trying out a range of values on 21 training images. $\alpha_{near}$ was then varied by up to 100% and $\alpha_{far}$ by up to 30% of their optimal values. The system output was robust with these variations.

Figure 14A:
FIGS. 14a-14d are images showing sample boundary definitions achieved by the present invention.
Figure 14B:
Figure 14C:
Figure 14D:
Figure 15:
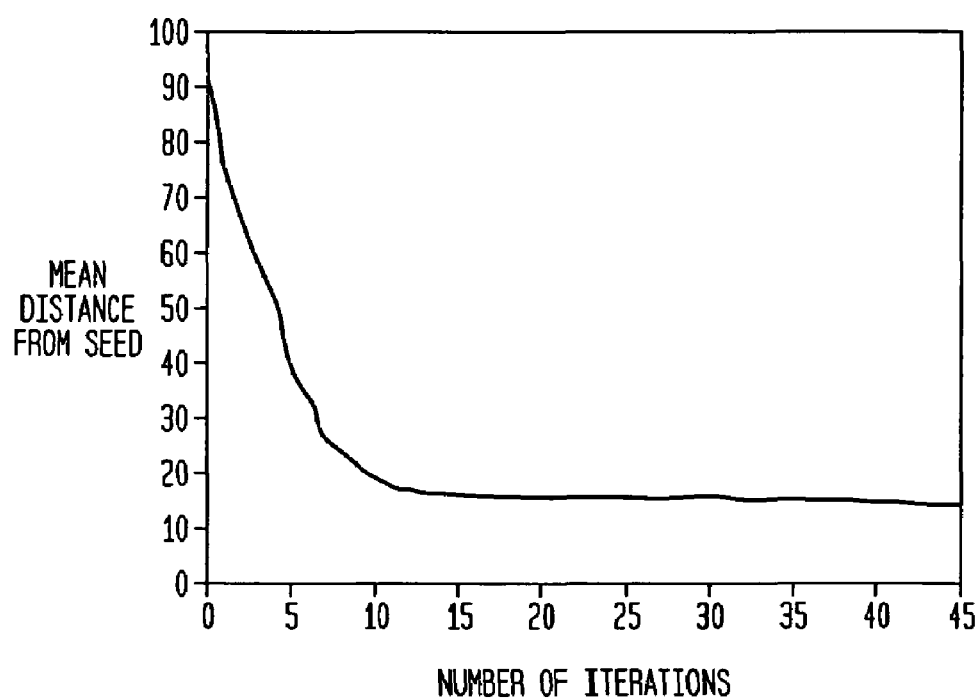
FIG. 15 is a graph showing a sample convergence of boundary points generated by the present invention.

FIGS. 14*a*-14*d* are images showing sample boundary definitions achieved by the present invention. FIG. 14*a* shows the original image. FIG. 14*b* shows the positions of the initial boundary points superimposed on the original image (bright pixels). The directional gradient image is shown in FIG. 14*c*, which reveals that the lower part of the lesion boundary actually lies above the shadow region. The arrow in FIG. 14*c* shows the position of the lower boundary of the tumor. As can be seen in FIG. 14*b*, some of the boundary points are detected incorrectly in the shadowing region. Still others are detected within the lesion area. After performing a recursive refinement, the local maxima in FIG. 14*b* are eliminated. The points converge to the boundary of the tumor region in FIG. 14*d*. No part of the shadow region has been included as belonging to the tumor. This result is remarkable considering that visually it is difficult to detect the lower boundary of the tumor. Convergence is determined as having occurred when the value of $\xi$ is less than $\partial=1.5$ pixels, and a sample convergence plot for boundary points is shown in FIG. 15.

After the boundary points have been determined, they are passed as inputs to a deformable model in step 100 of FIG. 1, which indicates in step 120 the presence or absence of a tumor. Deformable models such as snakes, active contours, and deformable superquadrics have become popular tools in image segmentation. Of late, they have become important in the medical imaging field. In these boundary-based methods, a shape model is initialized close to the object boundary. Image features are then used to fit the model to the boundary. To avoid local minima, most boundary-based methods require that the model be initialized near the solution and be controlled via an interactive user interface. Active contour models have in the past been applied to medical ultrasound images. However, in all of these techniques, an initial guess of the boundary or surface must be provided manually and placed close to the true contour. In the present invention, the boundary points are automatically detected for the initial contour, thereby avoiding manual intervention.

Preferably, the deformable model used in block 100 of FIG. 1 comprises a modified version of the physics-based deformable model disclosed in Metaxas, et al., "Image Segmentation Based on the Integration of Markov Random Fields and Deformable Models," The Third International Conference on Medical Image Computing and Computer-Assisted Intervention, 2000, pp. 256-265, the entire disclosure of which is expressly incorporated herein by reference. However, other models could be used. In the Metaxas, et al. deformable model, the reference shape is the set of nodes corresponding to the boundary points computed by the present invention. Given this reference shape r, and the displacement S (local deformation), the position of points p on the model is described by:

$$p = r + s \quad (16)$$

To keep the continuity of the model surface, a continuous loaded membrane deformation strain energy is imposed on the model. The model nodes move under the influence of external forces. The model dynamics are described by the first order Lagrangian method.

$$\dot{Q} + KQ = f \quad (17)$$

where K refers to the stiffness matrix of the model based on the strain energy, Q is a vector in which the parameters used to describe r and s are concatenated, and $f$ refers to the external forces. The deformable model is initialized to the boundary points determined by the present invention, and moves under the influence of $f$. The external forces used are the balloon forces proposed by Cohen, et al. in "A Finite Element Method Applied to New Active Contour Models and 3D Reconstruction From Cross Sections," International Conference on Computer Vision, 1990, pp.587-591, the disclosure of which is expressly incorporated herein by reference. The snake is attracted to contours with large image gradients, i.e., strong edges. However, when an image has a complex background, such as in sonographic images, the snake gets confused. Hence, finding the true object boundary from the gradient magnitude alone is not easy. Instead of using just the gradient magnitude, the balloon forces $f$ operate on the directional gradient of the contrast-enhanced image. Once the model reaches the estimated boundary, the associated nodes stop deforming. Nodal deformations are computed using finite elements. When most of the nodal points stop moving, the model stops deforming.

Experimental Results

The present invention was tested on a database of 48 images in QUICKTIME movie format from the Department of Radiology, Hospital at the University of Pennsylvania. These images were converted to individual JPEG images using MOVIECONVERTER on a SILICON GRAPHICS workstation. Out of a database of 48 images, 42 images were chosen for purposes of training and testing. Only those sonograms from the database in which the lesion could be manually identified by a trained radiologist were utilized. In the remaining six images, the expert radiologist was unable to distinguish the lesion area visually, and hence these were discarded. Of the 42 images left in the image database, half were randomly selected for training the intensity and texture classifier. The suspicious masses were identified and then manually delineated by a trained radiologist. The manually identified lesions were then cropped out from these 21 training images. This was done using PHOTOSHOP. The cropped lesions were used for generating the probability distribution functions for intensity and texture. The system was built using IDL 6.0 and tested on a database of 42 images. These 42 images included the 21 images that had been used for training. The images in the database contained cysts and lesions, both benign and malignant. Running time to extract the boundary of a single image was 18 seconds on a 1.8 GHz PENTIUM processor.

For detecting the boundary points in the gradient image, the radial lines were sampled at intervals of $\pi/180$. For the Butterworth filter, values of, $\phi=0.3$ and $\gamma=1.5$ and as described above gave the best results. N=9 was used for the number of neighboring pixels in the texture computation module. $\beta_1, \beta_2$ were set to 1 and 0.5, respectively, for the region growing operation. However, since this operation is only performed to get an approximate ROI containing the tumor region, the exact values of $\beta_1, \beta_2$ may vary. For scaling the result of region growing, $\epsilon=1.4$ was used. The values for the free parameters $N, \beta_1, \beta_2$ were decided upon empirically after varying their values and testing them on the training database of 21 images.

To validate the results, a radiologist manually delineated lesions in the images in the database. In 6 cases, the radiologist was unable to establish the ground truth, due to poor image quality. Hence, only 42 images were retained, and the other 6 discarded. Of the 42 images, the present invention produced results which showed very good agreement with the delineations of the radiologist.

Qualitative Results

Figure 16A:
FIGS. 16a-16d are images showing results of segmentation achieved by the present invention for a small tumor.
Figure 16B:
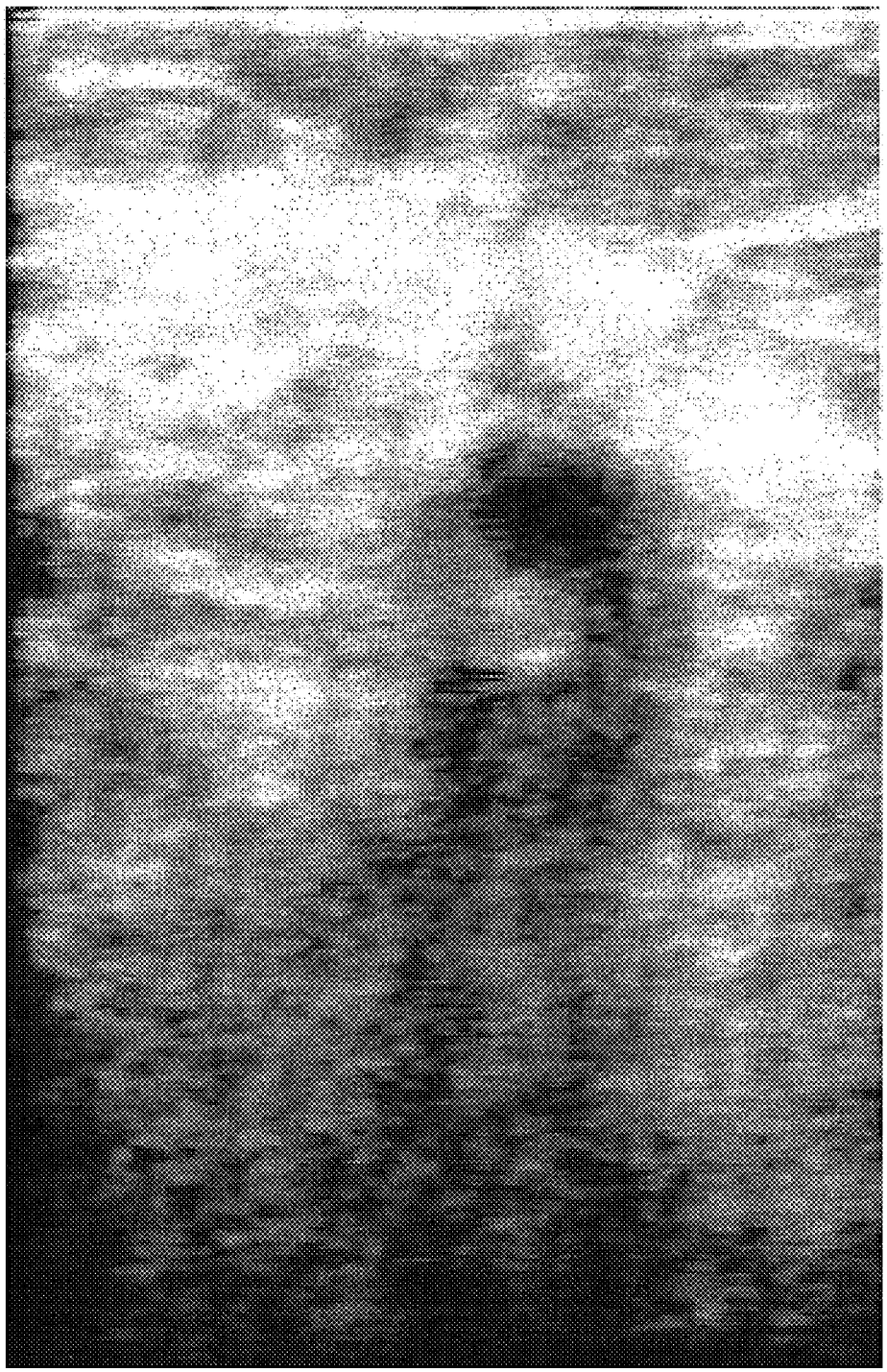
Figure 16C:
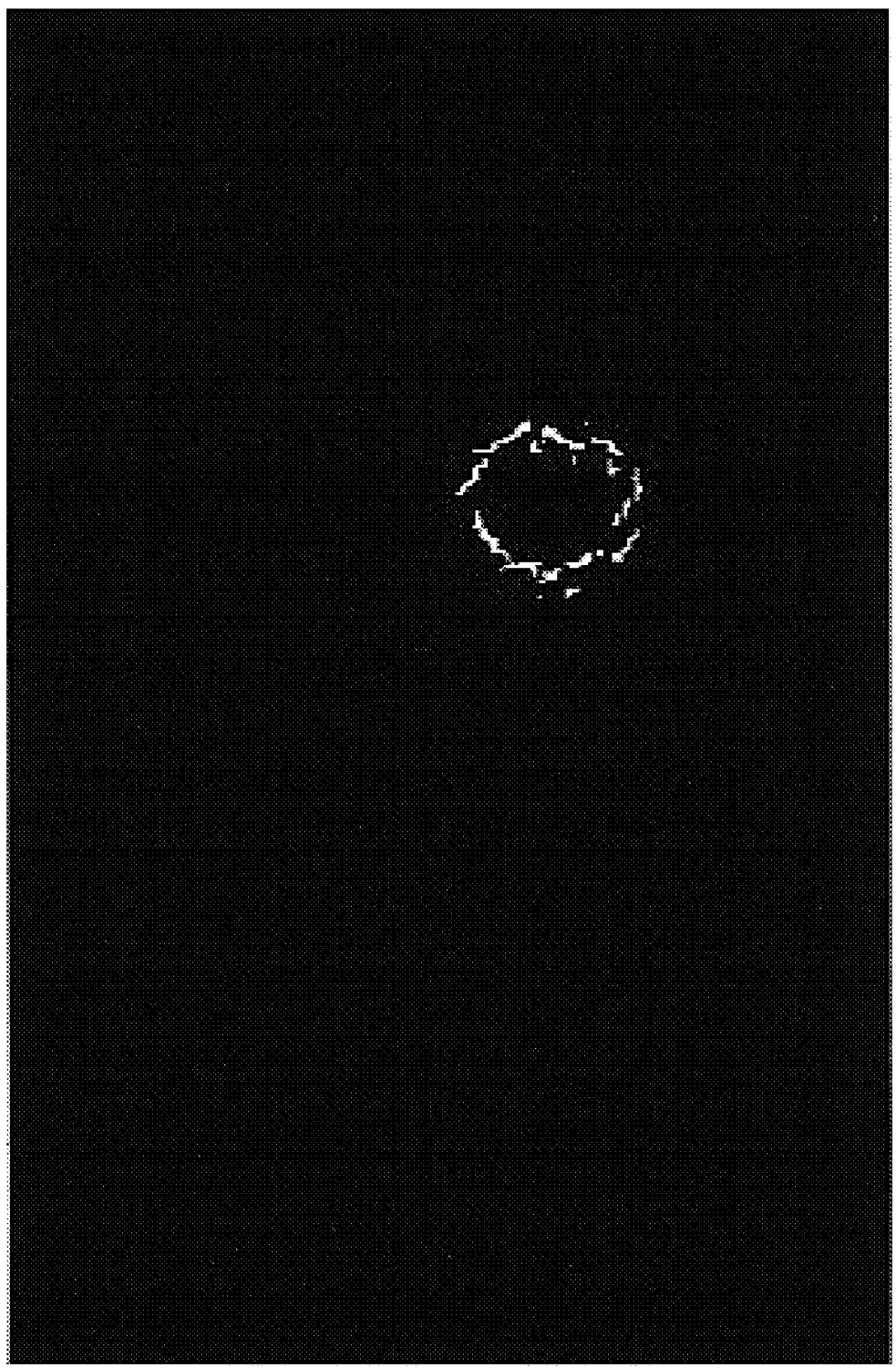
Figure 16D:
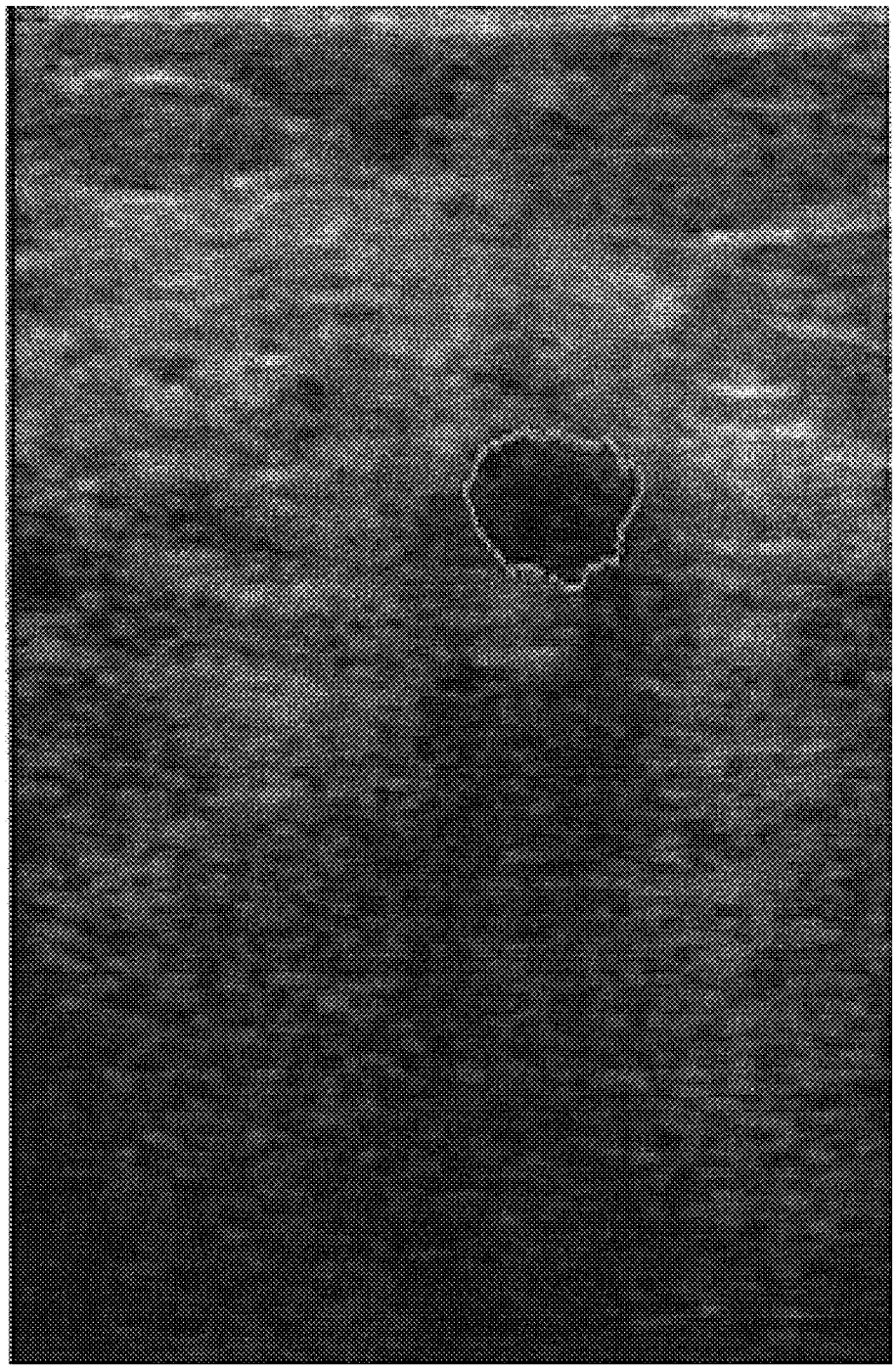
Figure 17A:
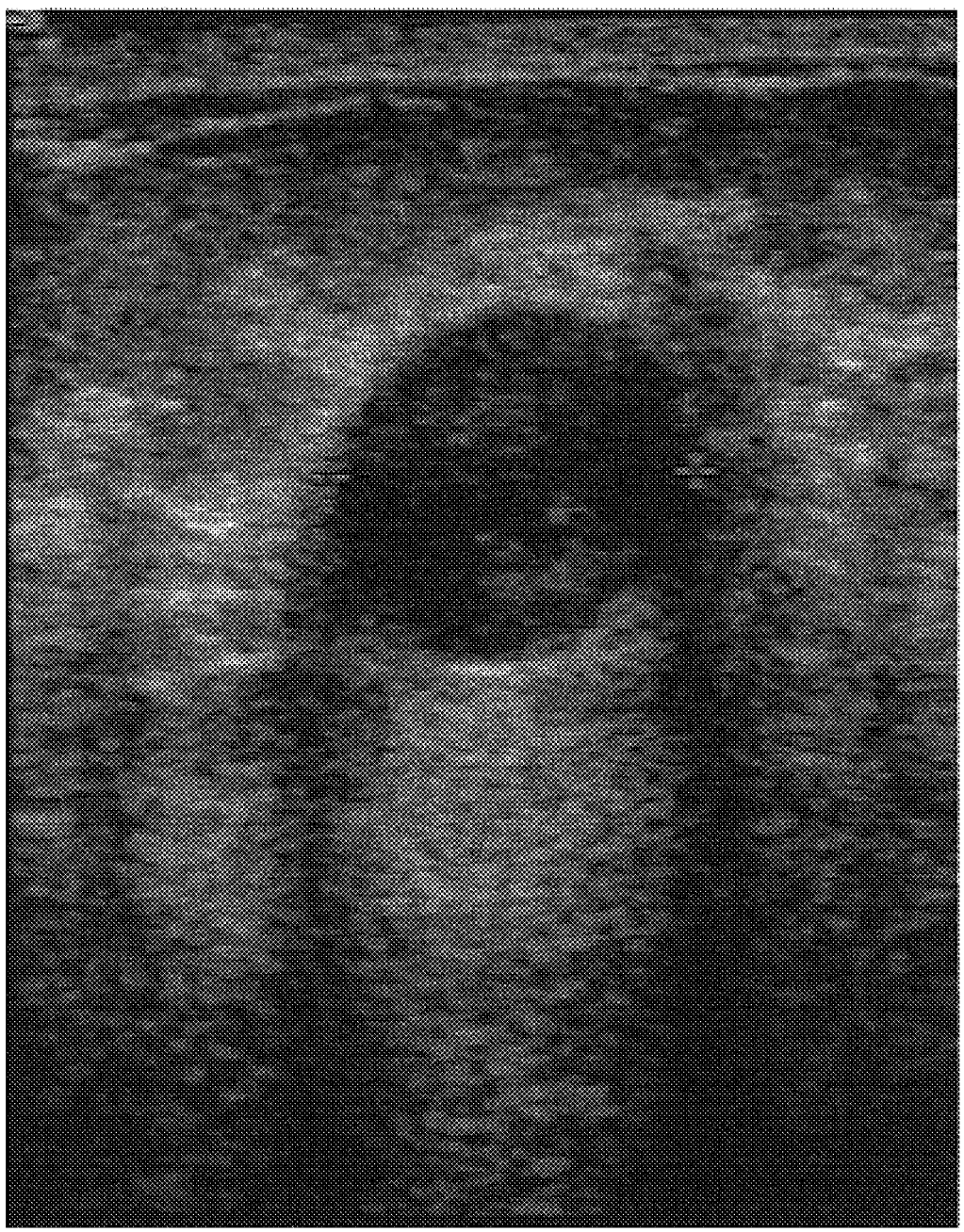
FIGS. 17a-17d are images showing results of segmentation achieved by the present invention for a large tumor.
Figure 17B:
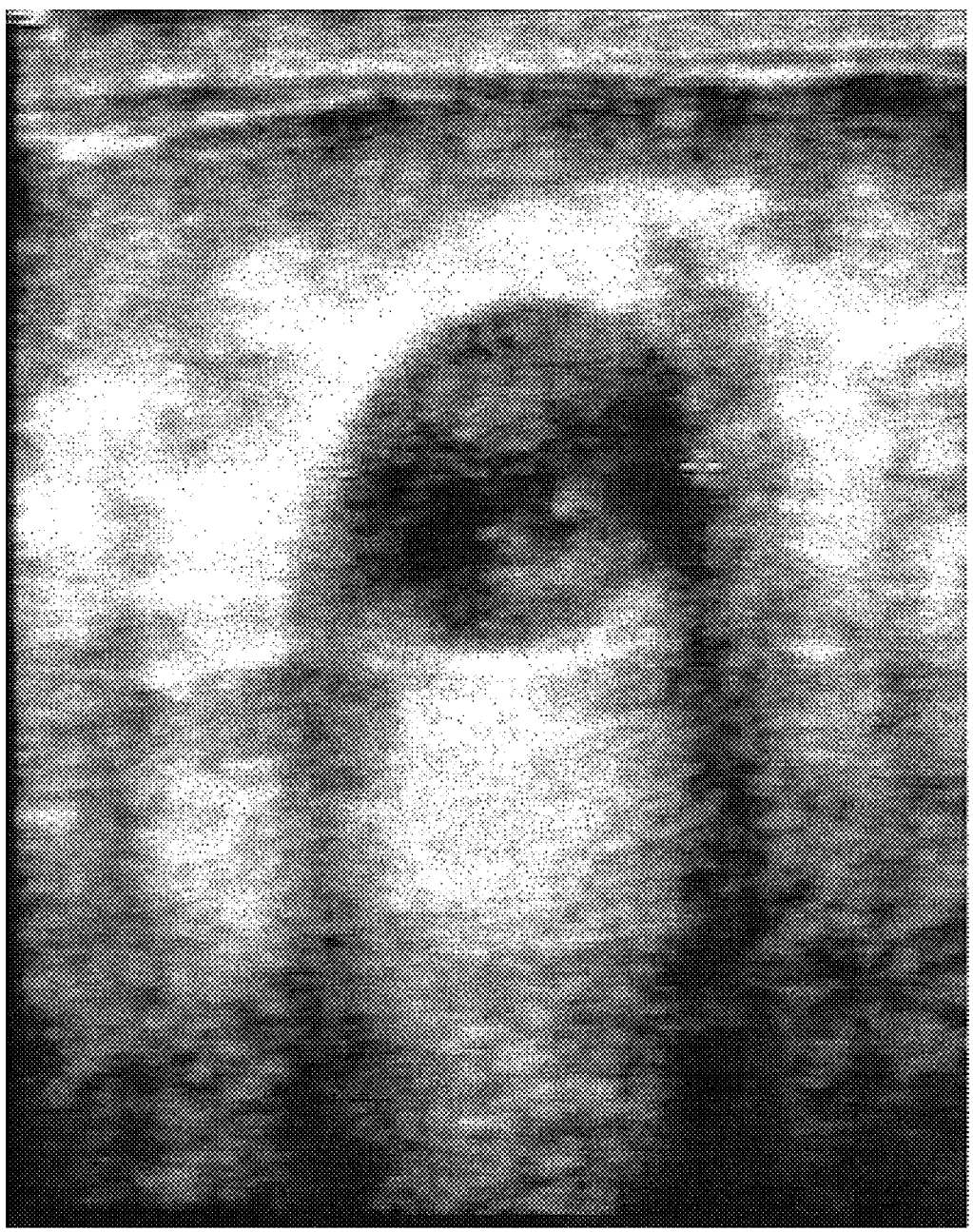
Figure 17C:
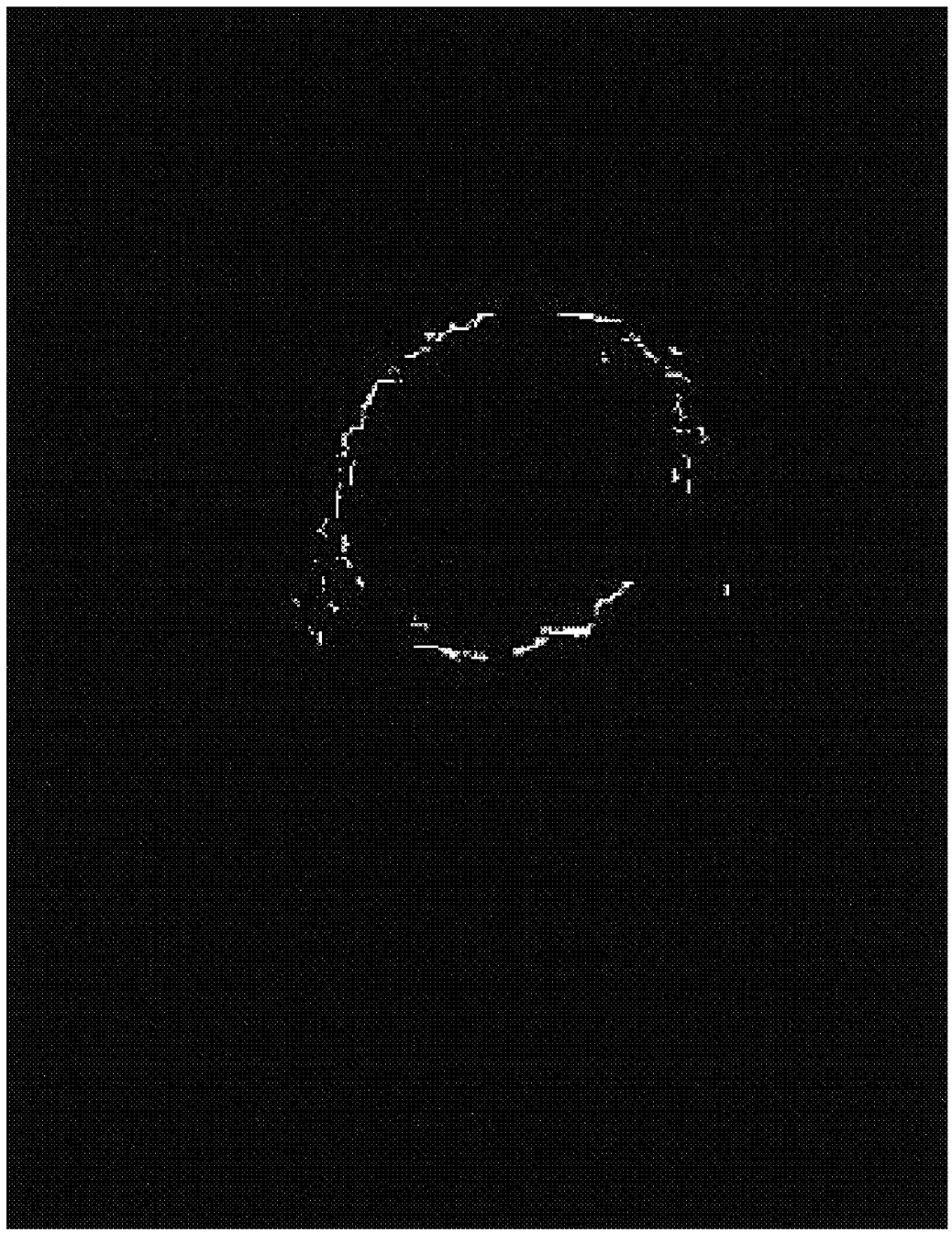
Figure 17D:
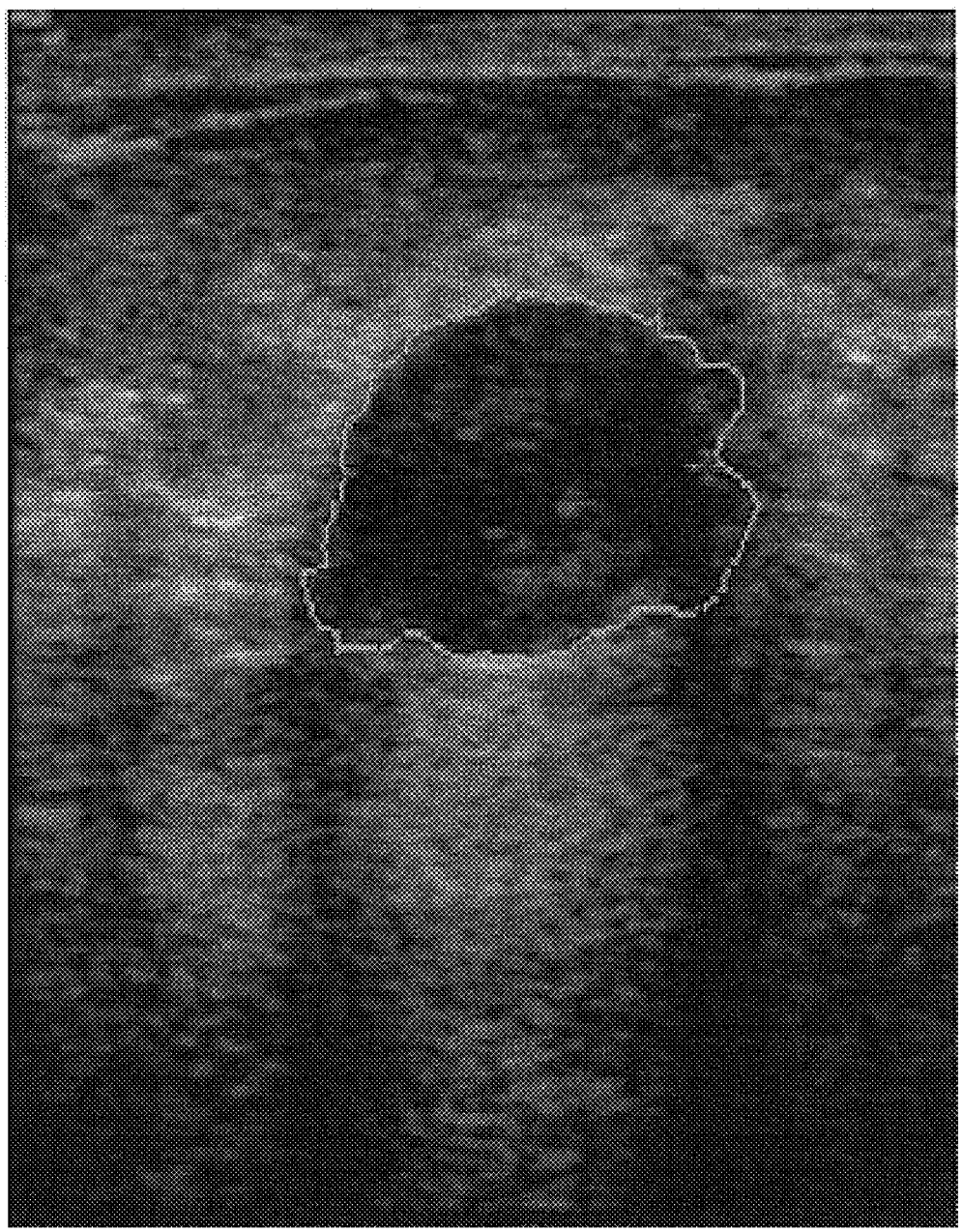
Figure 18A:
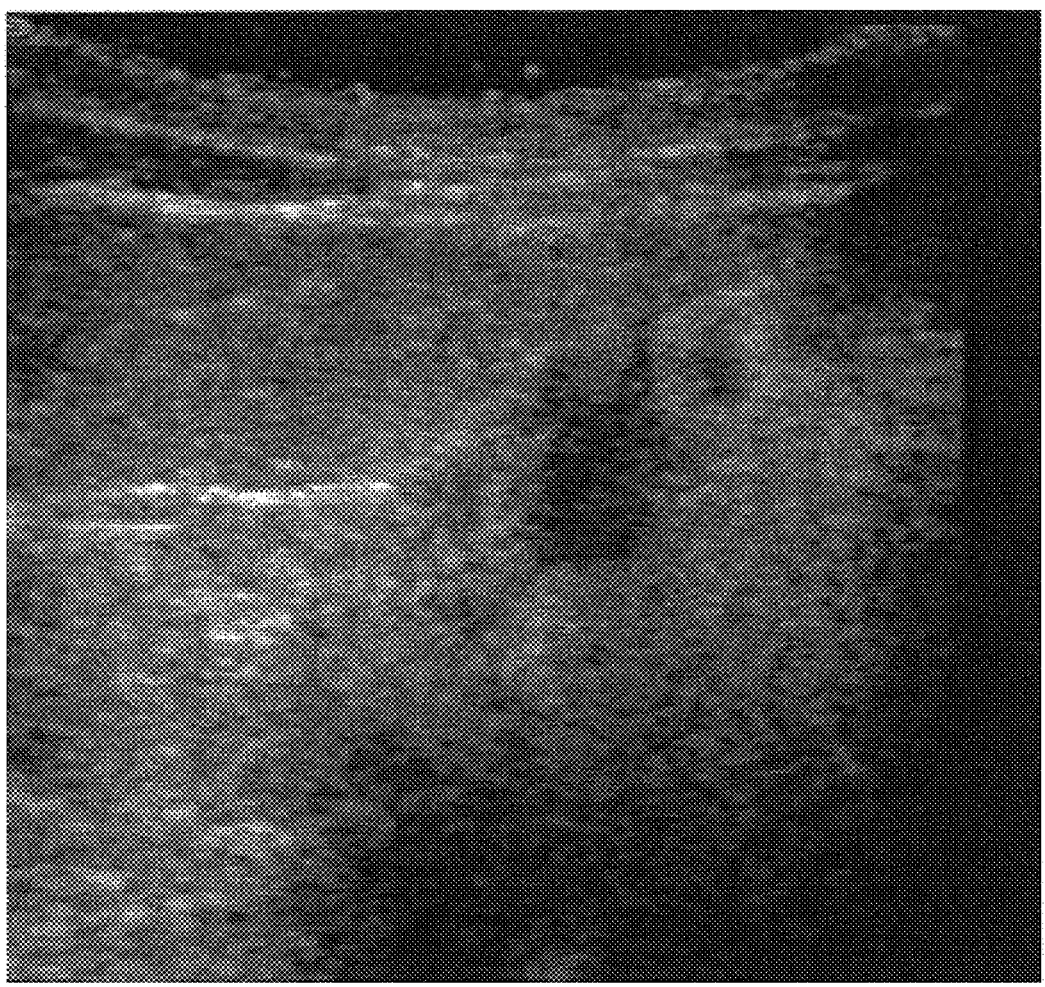
FIGS. 18a-18d are images showing results of segmentation achieved by the present invention for a tumor with poorly-defined margins.
Figure 18B:
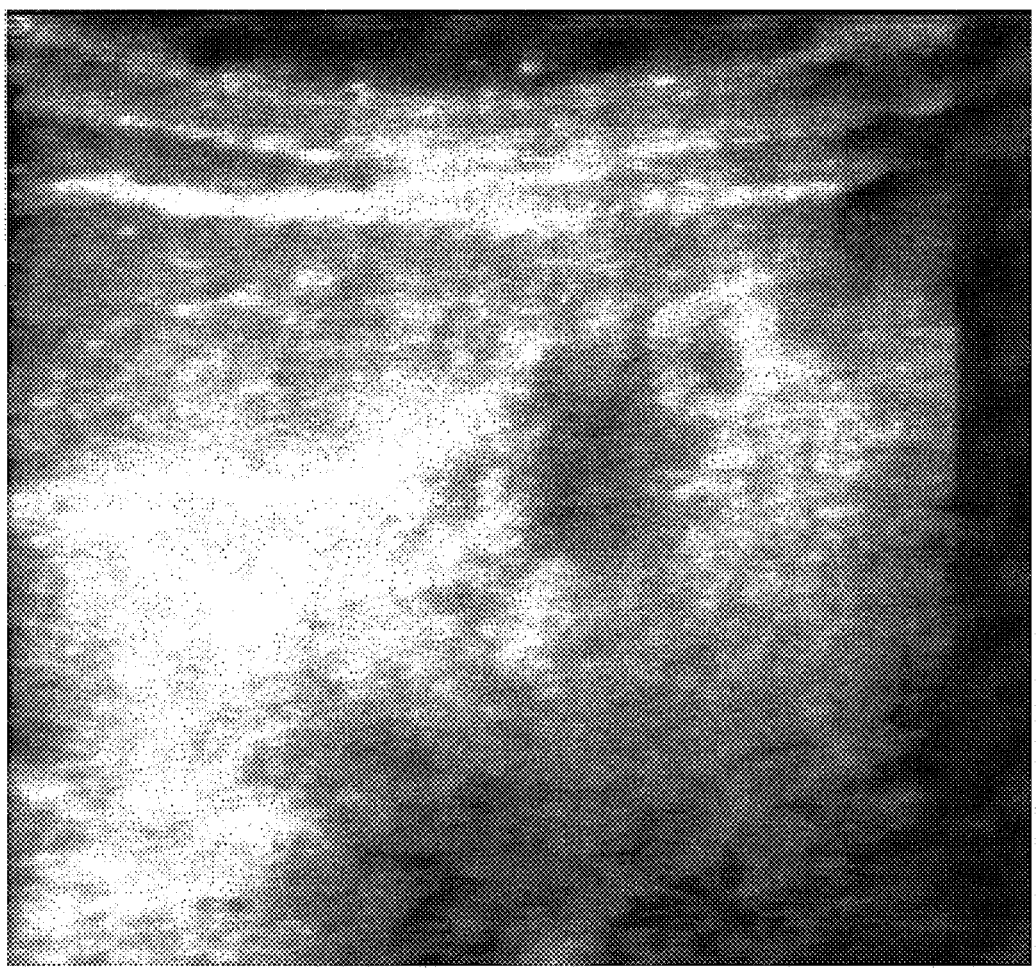
Figure 18C:
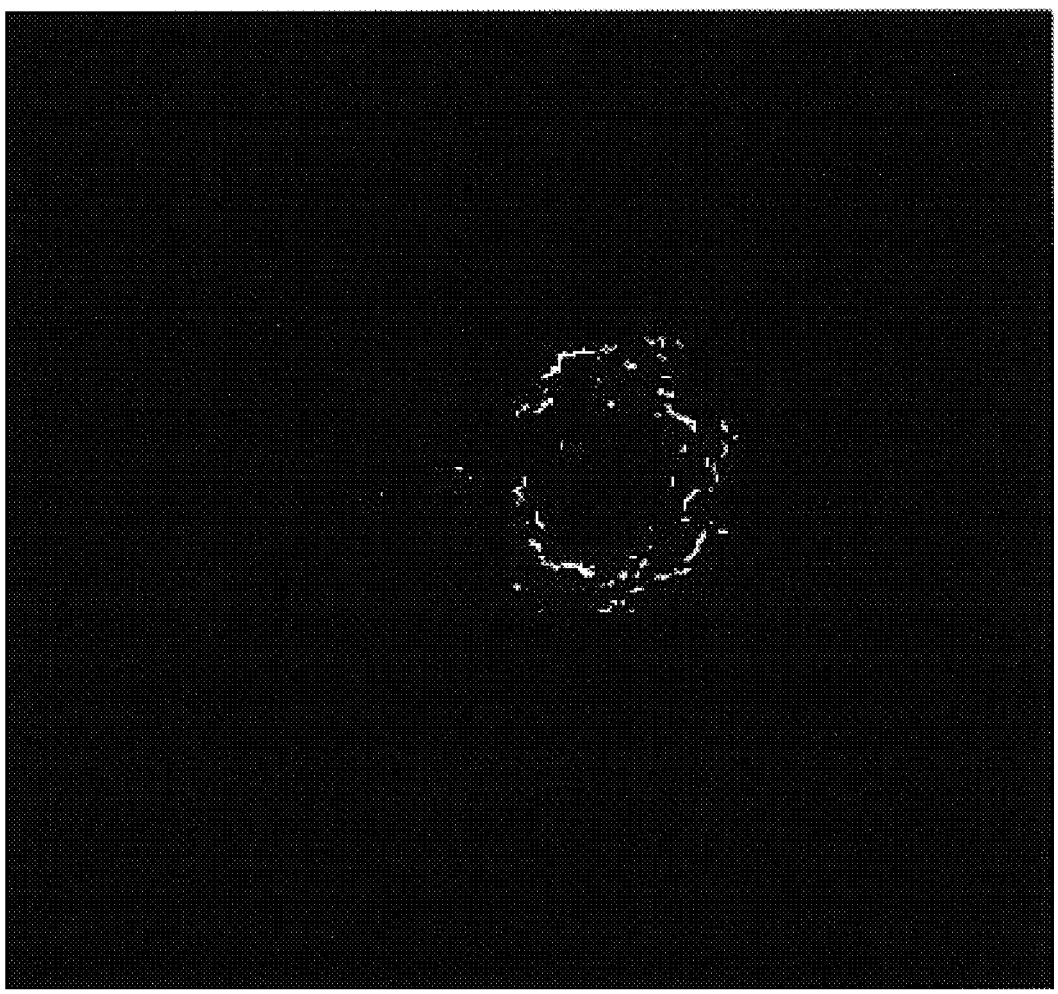
Figure 18D:
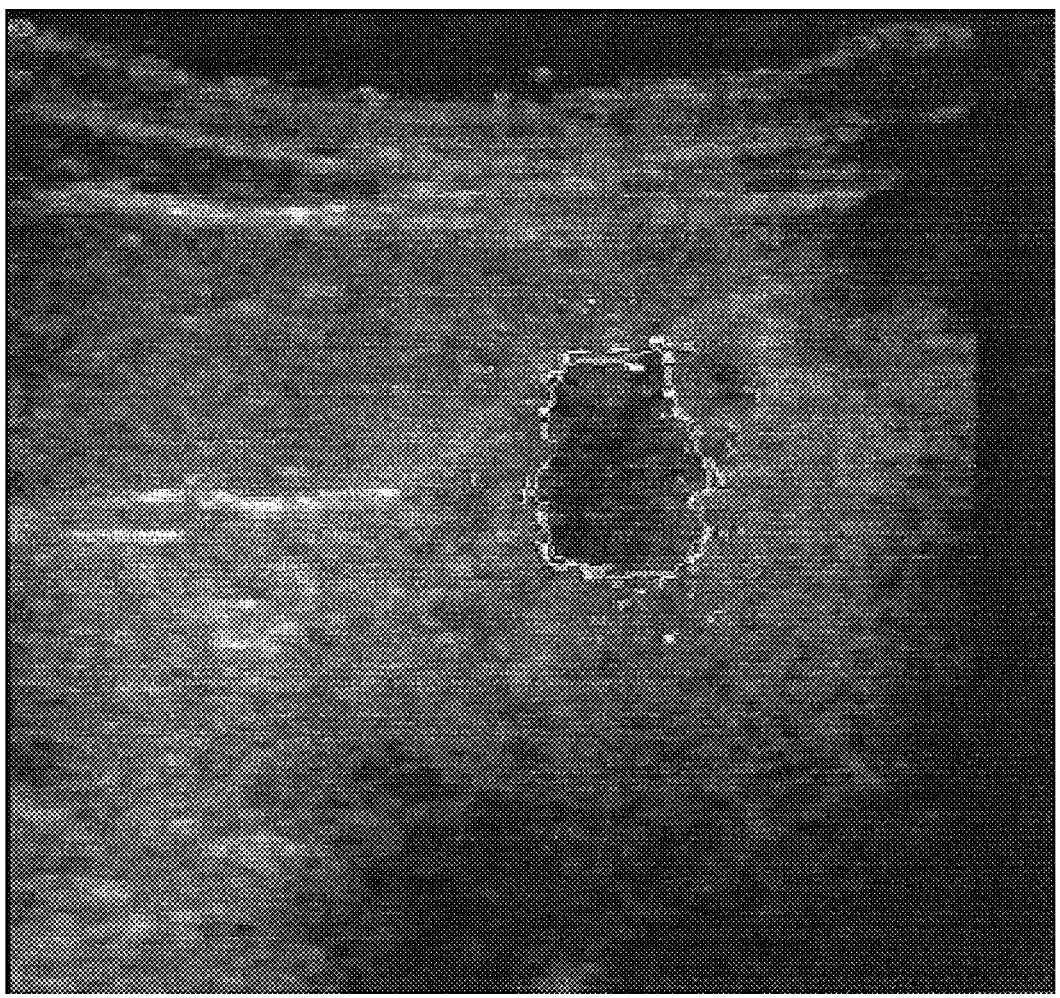

FIGS. 16a-16d, 17a-17d, and 18a-18d show the segmentation results of the present invention on three different ultrasound images. For each series of images, (a) is the original input image, (b) is the contrast enhanced version of (a), (c) is a binary image showing the position of the boundary points and supplied as an initial estimate to the deformable model, and (d) is the final output of the deformable model. A small tumor is shown in FIG. 16a. It is difficult to visually determine the boundary of this lesion. Despite the large amount of speckle, the present invention was able to accurately find the boundary points of the lesion. The deformable model, using the initial estimate shown in FIG. 16c, captured the true contour of the tumor in FIG. 16d.

In FIGS. 17a-17d, the present invention was able to detect most of the boundary points on a much larger tumor. Using the boundary points shown in FIG. 17c as the initial nodes, the deformable model accurately captured the margin of the lesion in FIG. 17d. The algorithm successfully avoided including the vertical dark lines on either side of the tumor, corresponding to posterior acoustic shadowing.

FIGS. 18a-18d show a tumor with poorly defined margins. The present invention was able to produce an accurate segmentation in spite of the poor definition of the boundary.

Further, potential outliers in the lower corners of the image and to the right of the tumor were avoided. The results displayed above show that the present invention was able to accurately segment out lesions of different shapes and sizes. Additionally, the present invention was able to discriminate the lesion area from the shadowing and the glandular and fatty tissue.

Quantitative Results

To evaluate the accuracy of the present invention, the automated results were quantitatively compared with the manual delineations produced by one expert radiologist. Two boundary-based error metrics were used to compare the automated and manual delineations of the lesion contour, including area and boundary metrics.

The two boundary error metrics used were the Hausdorff distance and the mean absolute distance. We denote the manually delineated boundary as $M=\{m_1, m_2, \ldots, m_n\}$ and the computer-aided segmentation result as $P=\{\rho_1, \rho_2, \ldots, \rho_o\}$, where each element of P or M is a point on the corresponding contour. We find the distance of every point in P from all points in M. We define the distance to the closest point for $\rho_j$ to the contour M as:

$$\forall \wp_j \in P \text{ we find} \tag{18}$$
$$d(\wp_j, M) = \min_{\omega} \|\wp_j - m_\omega\|$$

where $\|.\|$ is the two-dimensional (2D) Euclidean distance between any two points. The Hausdorff distance is defined as the maximum $d(\rho_j, M)$ over all j. The mean absolute distance is the average of $d(\rho_j, M)$ over all j. While the Hausdorff distance measures the worst possible disagreement between the two outlines, the mean absolute distance estimates the disagreement averaged over the two contours. If the Hausdorff error (HE) is found to be larger than the average mean error (ME), it shows that there are some outlier points on the automatically segmented boundary.

In Table 1 are listed the average Haussdorf (HE) and mean distance errors (ME) between the positions of the boundary pixels detected by the present invention and the manual delineations of a trained radiologist for $\alpha_{near}=0.6$ and $\alpha_{far}=1.45$ The average Haussdorf error for the database of 42 images was found to be 19.727 pixels and the average mean error was only 6.6 pixels. The corresponding normalized errors were computed by dividing HE and ME by the number of boundary pixels as determined in the manual segmentation. These were found to be 6.6% and 2.26% respectively. The tabulated results clearly indicate good correlation between the automated and manual segmentation results.

TABLE 1

| | Boundary errors for $\alpha_{near} = 0.6$ & $\alpha_{far} = 1.4$. | | | |
|---|---|---|---|---|
| Cases | HE | Avg. ME | Norm. HE | Norm. ME |
| 42 | 19.727 | 6.687 | 6.603 | 2.265 |

Figure 19:
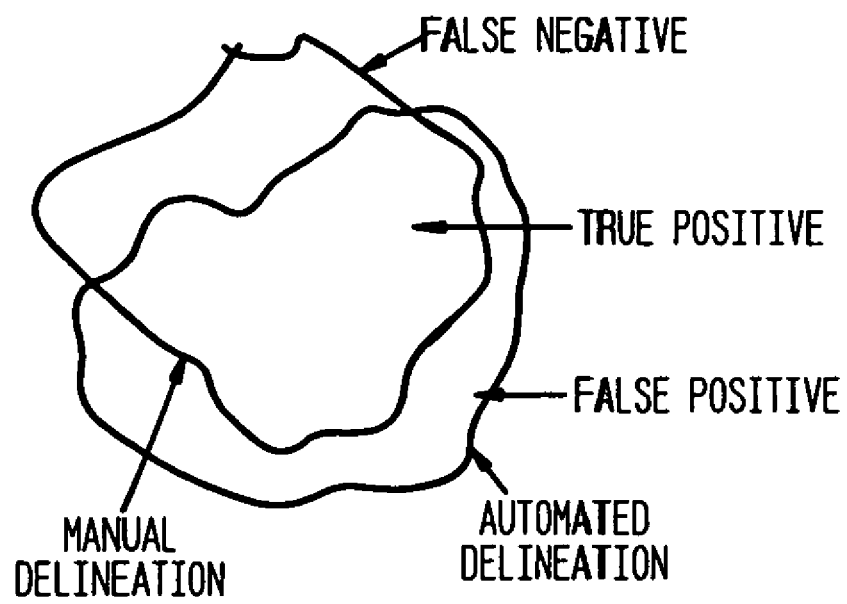
FIG. 19 is a graph showing area error metrics illustrating accuracy of the present invention.

To measure area metrics, three metrics were established to find the difference in estimates between the manual and automatically delineated areas. We defined the False Positive (FP), False Negative (FN) and True Positive (TP) areas as:

$$FP = \frac{|A_a \cup A_m - A_m|}{A_m} \tag{19}$$

$$FN = \frac{|A_a \cup A_m - A_m|}{A_m} \tag{20}$$

$$TP = \frac{|A_a \cap A_m|}{A_m} \tag{21}$$

where $A_m$ refers to the area of the tumor as determined by manual segmentation and $A_a$ is the area of the lesion determined by the present invention. FIG. 19 shows the areas corresponding to FP, FN and TP.

Table 2 lists the mean of the error in area for all the images in the dataset. The average percentage of normal pixels which were classified as tumor was 20.86% while the percentage of tumor pixels that were not detected by the present invention was 24.9%. The average true positive percentage was 75.1%. All but two of the images in the database had a true positive percentage over 50%. The mean true positive percentage of the best 40 images in the database was 78%. The two images that were ignored while computing this statistic belonged to the training dataset.

TABLE 2

| Errors in segmented area for $\alpha_{near} = 0.6$ & $\alpha_{far} = 1.45$. | | | |
|---|---|---|---|
| Cases | FP % | FN % | TP % |
| 42 | 20.856 | 24.959 | 75.041 |

Sensitivity Analysis

A segmentation algorithm can only be called robust if its performance is almost insensitive to variation of its parameters. Sensitivity analysis is an important component in the evaluation of the overall performance of a segmentation system. Three different factors for evaluating segmentation methods include precision (reproducibility), accuracy, and efficiency.

As mentioned earlier, outliers are eliminated by the present invention from the set of boundary points by using distance thresholds $\alpha_{near}$ and $\alpha_{far}$. Hence, by changing the values of these two parameters, points would be closer or farther from the seed point. Consequently, the set of points supplied to the deformable model would change and result in a different segmentation. To determine how different the final segmentation result would be, $\alpha_{near}$ and $\alpha_{far}$ were varied and computed the resulting Haussdorf (HE) and mean distance errors (ME).

The intensity and texture classifier module of the present invention was trained on a set of 21 images. These were selected from the original database of 42 breast sonograms. The training module assigned individual image pixels probabilities of belonging to a tumor based on their texture and intensity values. The 21 training images were chosen randomly from the database in order to not bias the system performance. To investigate whether the 21 images constituted a representative database for classification, the training set was expanded by incorporating 11 more images. The segmentation results obtained using this larger training set were compared with those obtained using the original training set of 21 images. This was done to evaluate system sensitivity to the number of training samples.

Correctly determining the seed point within the lesion area is a prerequisite to getting an accurate segmentation. However, since the present invention selects the seed from a random set of points in the image, the seed point position changes every time the program is run. To determine how the precise location of the seed point would affect the final segmentation, its position was varied within the lesion area and computed the resulting Hausdorff distance (HE) and the average mean distance errors (HE).

A database of 48 breast sonograms was provided to determine the effects of increased training. In 6 of these images, the radiologist was unable to identify the lesion site. Of the remaining 42 images left in the database, 21 were used for training. The system performance using these 21 training images are listed in Tables 3 and 4. To investigate whether segmentation performance would be enhanced by increasing the number of training samples, the present invention was also trained on 32 training images, i.e., $3/4^{th}$ of the database.

TABLE 3

Boundary errors using 32 training samples with $\alpha_{near} = 0.6$ & $\alpha_{far} = 1.4$.

| Cases | HE | Avg. ME | Norm. HE | Norm. ME |
|---|---|---|---|---|
| 42 | 18.435 | 5.600 | 6.18 | 1.95 |

TABLE 4

Errors in segmented area using 32 training samples with $\alpha_{near} = 0.6$ & $\alpha_{far} = 1.45$.

| Cases | FP % | FN % | TP % |
|---|---|---|---|
| 42 | 21.376 | 23.937 | 76.067 |

Comparing the results in Tables 3 and 4 with those in Tables 1 and 2, it can be noticed that the average area and boundary errors for the entire dataset of 42 images had decreased slightly by increasing the number of training samples to 32. For the same values of $\alpha_{near}$ and $\alpha_{far}$ the average Haussdorf and mean boundary error over the entire database was reduced by 1.4 and 1.08 pixels respectively. The average true positive area percentage increased by 1.02% by expanding the training set. To determine whether these changes were statistically significant over the entire database, the boundary and area errors were compared using the two different training sets via a paired t-test. The t-test was performed under the null hypothesis that there is a decrease in TP %, FP % and the Haussdorf and mean boundary errors using the training set containing 32 images. The hypothesis was rejected at a significance level of $P<0.05$ indicating that the decrease was not statistically significant. The p values from the t-test are listed in Table 5. The p values for both the area and error metrics were greater than 0.05 indicating that the slight increase in performance using the larger training set was not statistically significant.

The system was also tested using a smaller training database (i.e. 10 images). However, the system performance was significantly worse when using $1/4^{th}$ of the images in the database for training.

TABLE 5 p values for paired student t-test on area and boundary errors for the two training sets.

| TP % | FP % | HE | ME |
|---|---|---|---|
| 0.2015 | 0.2111 | 0.098 | 0.1037 |

The images in the database that had not been included in the training dataset were also separately analyzed. This was done to see whether these images performed worse than the training images. For the first training set containing 21 training images, the area and boundary errors for the remaining 21 of the 42 sonograms in the database were computed. Hence, both the test and training datasets contained 21 images. For the second training set containing 32 images, the corresponding test dataset contained 10 images (42−32=10). The average boundary and area errors for the results generated using the training set containing 21 and 32 sonograms respectively are listed in Tables 6 and 7, respectively. For the first training set of 21 images, the average performance of the 21 test images was better than that of the training sonograms with respect to the boundary error metrics. In terms of the area error metric, the 21 test images had a lower false positive % area than the training images. But, the training images performed marginally better than the test images in terms of true positive % area. For the second dataset containing 32 training images, the results were similar to those obtained with the first training set. The average Haussdorf and mean boundary errors were lower for the 10 test images compared to the 32 training images. The average false positive % and true positive % areas for the training images however were better than that for the 10 test images.

TABLE 6

Boundary errors for test images using 21 & 32 training samples ($\alpha_{near} = 0.6$ & $\alpha_{far} = 1.4$).

| Cases | HE | Avg. ME | Norm. HE | Norm. ME |
|---|---|---|---|---|
| 21 | 17.4568 | 5.579 | 6.58 | 2.118 |
| 10 | 13.436 | 4.294 | 5.280 | 1.734 |

TABLE 7

Errors in segmented area for test images using 21 & 32 training samples ($\alpha_{near} = 0.6$ & $\alpha_{far} = 1.45$).

| Cases | FP % | FN % | TP % |
|---|---|---|---|
| 21 | 13.380 | 25.293 | 74.707 |
| 10 | 25.168 | 25.891 | 74.108 |

Based on the above results, the following conclusions can be made: (i) the training database of 21 images contained enough representative images in order to be able to accurately segment the lesions for the corresponding test images; (ii) increasing the number of training samples to 32 did not significantly improve the performance of the system; and (iii) the test images (entire dataset—training dataset) performed as well as the images in the training dataset. This is true for both training datasets.

The seed point position in the horizontal and vertical directions within the lesion were also varied, and the corresponding boundary error metrics were computed. The results are tabulated in Tables 8 and 9. In Table 8 lists the errors in boundary position by varying the seed point by a horizontal distance ($\Delta x$), and the corresponding results by varying the seed point by a vertical displacement ($\Delta y$) are listed in Table 9.

TABLE 8

Boundary errors for variation in seed point position (horizontal direction) for $\alpha_{near} = 0.6$ & $\alpha_{far} = 1.4$.

| $\Delta x$ | Avg. HE | Avg. ME | Norm. HE | Norm. ME |
|---|---|---|---|---|
| +2 | 19.99 | 6.951 | 6.684 | 2.326 |
| +1 | 19.727 | 6.687 | 6.603 | 2.265 |
| −2 | 20.266 | 6.966 | 6.674 | 2.307 |
| −1 | 19.907 | 7.071 | 6.653 | 2.369 |

TABLE 9

Boundary errors for variation in seed point position (vertical direction) for $\alpha_{near} = 0.6$ & $\alpha_{far} = 1.4$.

| $\Delta y$ | Avg. HE | Avg. ME | Norm. HE | Norm. ME |
|---|---|---|---|---|
| +2 | 21.056 | 7.399 | 6.903 | 2.435 |
| +1 | 20.615 | 7.295 | 6.806 | 2.418 |
| −2 | 21.056 | 7.399 | 6.904 | 2.435 |
| −1 | 20.615 | 7.295 | 6.806 | 2.418 |

The standard deviation in error for the Haussdorf and mean average distance by varying $\Delta x$ was 0.2242 and 0.1636 pixels respectively, as shown in Table 10. Similarly, the standard deviation in error for the two distance metrics obtained by varying $\Delta y$ was 0.5338 and 0.2342 pixels respectively. The small standard deviations showed that the system was not dependent on the precise location of the seed point within the lesion.

TABLE 10

Standard Deviation in errors with variation of $\Delta x$ & $\Delta y$.

| Parameter Variation | ME | HE |
|---|---|---|
| $\Delta x$ | 0.1636 | 0.2242 |
| $\Delta y$ | 0.2342 | 0.5338 |

Having thus described the invention in detail, it is to be understood that the foregoing description is not intended to limit the spirit and scope thereof. What is desired to be protected by Letters Patent is set forth in the appended claims.

What is claimed is:

1. A method for automatically detecting breast tumors and lesions in an image comprising:
   acquiring an image of a breast;
   filtering the image;
   applying texture and intensity classifiers to each pixel of the image, the classifiers corresponding to probabilities of the pixel belonging to a lesion or tumor;
   determining a seed point in the image by retrieving a set of points of interest in the image, selecting a first point from the set of points, calculating a joint probability that the first point corresponds to a tumor, calculating mean joint probabilities that points in a circular region around the first point correspond to a tumor, and designating a point within the circular region having a maximum mean joint probability as the seed point;
   growing a region of interest around the seed point;
   calculating directional gradients for each pixel in the image;
   determining boundary points of the region of interest using the directional gradients; and
   processing the boundary points with a deformable model to determine the presence or absence of a tumor or lesion in the image.

2. The method of claim 1, wherein the step of acquiring the image comprises digitizing the image from an analog mammogram.

3. The method of claim 1, wherein the step of acquiring the image comprises acquiring a digital mammogram, ultrasound, or MRI image of a breast.

4. The method of claim 1, wherein the step of filtering the image comprises removing speckle from the image using a Butterworth filter.

5. The method of claim 4, further comprising enhancing contrast of the image.

6. The method of claim 1, wherein the step of applying texture and intensity classifiers comprises determining intensity and local variance of each pixel of the image.

7. The method of claim 6, further comprising applying a texture probability distribution function to the local variance of the pixel to produce the texture classifier.

8. The method of claim 6, further comprising applying an intensity probability distribution function to the intensity of the pixel to produce the intensity classifier.

9. The method of claim 1, wherein the step of growing the region of interest comprises:
   adding the seed point to the region of interest; and
   adding pixels to the region of interest based upon connectivity and values of surrounding pixels.

10. The method of claim 1, wherein the step of determining boundary points comprises scanning the region of interest horizontally and vertically to determine edge points, and combining the edge points.

11. The method of claim 10, further comprising drawing radial lines from the seed point and plotting boundary points corresponding to positions of maximum intensity on the radial lines.

12. The method of claim 11, further comprising removing outliers and local maxima from the boundary points.

13. An apparatus for automatically detecting breast tumors and lesions in an image comprising:
   a scanner for generating an image of a breast;
   a filter for filtering the image;
   texture and intensity classifiers applied to each pixel of the image, the classifiers corresponding to probabilities of the pixel belonging to a lesion or tumor;
   means for determining a seed point in the image, wherein said means retrieves a set of points of interest in the image, selects a first point from the set of points, and calculates a joint probability that the first point corresponds to a tumor;
   means for growing a region of interest around the seed point;
   means for calculating directional gradients for each pixel in the image;
   means for determinimg boundary points of the region of interest using the directional gradient; and
   a deformable model for processing the boundary points to determine the presence or absence of a tumor or lesion in the image, wherein the means for determining the seed point calculates mean joint probabilities that points in a circular region around the first point correspond to a tumor.

14. The apparatus of claim 13, wherein the scanner comprises an analog mammogram scanner, a digital mammogram scanner, an ultrasound scanner, or an MRI scanner.

15. The apparatus of claim 13, wherein the filter comprises a Butterworth filter for removing speckle from the image.

16. The apparatus of claim 13, wherein the texture and intensity classifiers are generated by texture and intensity probability distribution functions applied to pixels of the image.

17. The apparatus of claim 13, wherein the means for determining the seed point designates a point within the circular region having a maximum mean joint probability as the seed point.

18. The apparatus of claim 13, wherein the means for growing the region of interest adds the seed point to the region of interest and adds pixels to the region of interest based upon connectivity and values of surrounding pixels.

19. The apparatus of claim 13, wherein the means for determining boundary points scans the region of interest horizontally and vertically to determine edge points, and combines the edge points.

20. The apparatus of claim 19, wherein the means for determining boundary points draws radial lines from the seed point and plots boundary points corresponding to positions of maximum intensity on the radial lines.

21. The apparatus of claim 20, wherein the means for determining the boundary points removes outliers and local maxima from the boundary points.

22. A method for automatically detecting breast tumors and lesions in an image comprising:
    acquiring an image of a breast;
    filtering the image; applying texture and intensity classifiers to each pixel of the image, the classifiers corresponding to probabilities of the pixel belonging to a lesion or tumor;
    determining a seed point in the image;
    growing a region of interest round the seed point; calculating directional gradients for each pixel in the image;
    determining boundary points of the region of interest using the directional gradients by scanning the region of interest horizontally and vertically to determine edge points, and combining the edge points;
    drawing radial lines from the seed point and plotting boundary points corresponding to positions of maximum intensity on the radial lines; and
    processing the boundary points with a deformable model to determine the presence or absence of a tumor or lesion in the image,
    wherein the step of determining the seed point comprises:
        retrieving a set of points of interest in the image;
        selecting a first point from the set of points:
        calculating a joint probability that the first point corresponds to a tumor:
        calculating mean joint probabilities that points in a circular region around the first point correspond to a tumor: and
        designating a point within the circular region having a maximum mean joint probability as the seed point.

23. The method of claim 22, wherein the step of acquiring the image comprises digitizing the image from an analog mammogram.

24. The method of claim 22, wherein the step of acquiring the image comprises acquiring a digital mammogram, ultrasound, or MRI image of a breast.

25. The method of claim 22, wherein the step of filtering the image comprises removing speckle from the image using a Butterworth filter.

26. The method of claim 25, further comprising enhancing contrast of the image.

27. The method of claim 22, wherein the step of applying texture and intensity classifiers comprises determining intensity and local variance of each pixel of the image.

28. The method of claim 27, further comprising applying a texture probability distribution function to the local, variance of the pixel to produce the texture classifier.

29. The method of claim 22, further comprising applying an intensity probability distribution function to the intensity of the pixel to produce the intensity classifier.

30. The method of claim 22, wherein the step of growing the region of interest comprises:
    adding the seed point to the region of interest; and
    adding pixels to the region of interest based upon connectivity and values of surrounding pixels.

31. The method of claim 22, further comprising removing outliers and local maxima from the boundary points.

32. An apparatus for automatically detecting breast tumors and lesions in an image comprising:
    a scanner for generating an image of a breast;
    a filter for filtering the image;
    texture and intensity classifiers applied to each pixel of the image, the classifiers corresponding to probabilities of the pixel belonging to a lesion or tumor;
    means for determining a seed point in the image;
    means for growing a region of interest around the seed point;
    means for calculating directional gradients for each pixel in the image;
    means for determining boundary points of the region of interest using the directional gradients, the means drawing radial lines from the seed point and plots boundary points corresponding to positions of maximum intensity on the radial lines; and
    a deformable model for processing the boundary points to determine the presence or absence of a tumor or lesion in the image,
    wherein the means for determining the seed point retrieves a set of points of interest in the image, selects a first point from the set of points. calculates a joint probability that the first point corresponds to a tumor, and calculates mean joint probabilities that points in a circular region around the first point correspond to a tumor.

33. The apparatus of claim 32, wherein the scanner comprises an analog mammogram scanner, a digital mammogram scanner, an ultrasound scanner, or an MRI scanner.

34. The apparatus of claim 32, wherein the filter comprises a Butterworth filter for removing speckle from the image.

35. The apparatus of claim 32, wherein the texture and intensity classifiers are generated by texture and intensity probability distribution functions applied to pixels of the image.

36. The apparatus of claim 32, wherein the means for determining the seed point designates a point within the circular region having a maximum mean joint probability as the seed point.

37. The apparatus of claim 32, wherein the means for growing the region of interest adds the seed point to the region of interest and adds pixels to the region of interest based upon connectivity and values of surrounding pixels.

38. The apparatus of claim 32, wherein the means for determining boundary points scans the region of interest horizontally and vertically to determine edge points, and combines the edge points.

39. The apparatus of claim 32, wherein the means for determining the boundary points removes outliers and local maxima from the boundary points.

* * * * *

UNITED STATES PATENT AND TRADEMARK OFFICE
CERTIFICATE OF CORRECTION

| | | |
|---|---|---|
| PATENT NO. | : 7,466,848 B2 | Page 1 of 2 |
| APPLICATION NO. | : 10/736455 | |
| DATED | : December 16, 2008 | |
| INVENTOR(S) | : Dimitris N. Metaxas and Anant Madabhushi | |

It is certified that error appears in the above-identified patent and that said Letters Patent is hereby corrected as shown below:

In the References Cited Section, under Other Publications listed on Page 2 of the patent, the spelling of the author's name for the fourth reference listed should read "Boukerroui, et al." instead of "Boulerroui, et al."

Column 5, line 48, the equation should read "$\Psi(a,b) = \gamma(\varphi)\varphi\rho(a,b) + e^{-\varphi}\Psi(a-1,b);$"

Column 10, line 39, in the equation, the "$\partial$" should be deleted and replaced with "ñ;"

Column 10, line 41, "$\partial$" should be deleted and replaced with "ñ;"

Column 10, line 64, "$\partial$" should be deleted and replaced with "ñ;"

Column 13. line 20, "$P=\{\rho_1,\rho_2,\ldots,\rho\sigma\}$" should be deleted and replaced with "$P = \{\wp_1, \wp_2, \ldots, \wp_\sigma\};$"

Column 13, line 23, "$\rho_j$;" should be deleted and replaced with "$\wp_j;$"

Column 13, lines 35 and 36, "$\rho_j$;" should be deleted and replaced with "$\wp_j;$"

Column 15, line 15, there should be a space between the number "3" and the word "and;"

Column 19, line 35, after the semicolon, the paragraph should be moved to the next line Column 19, line 40, after the semicolon, the paragraph should be moved to the next line Column 20, line 11, the comma after the word "local" should be deleted; and

UNITED STATES PATENT AND TRADEMARK OFFICE
CERTIFICATE OF CORRECTION

PATENT NO. : 7,466,848 B2
APPLICATION NO. : 10/736455
DATED : December 16, 2008
INVENTOR(S) : Dimitris N. Metaxas and Anant Madabhushi It is certified that error appears in the above-identified patent and that said Letters Patent is hereby corrected as shown below:

Column 20, line 13, "22" should be deleted and replaced with "27."

Signed and Sealed this

Thirteenth Day of October, 2009

David J. Kappos
*Director of the United States Patent and Trademark Office*